(12) United States Patent
Galen et al.

(10) Patent No.: US 10,375,909 B2
(45) Date of Patent: *Aug. 13, 2019

(54) DIAGNOSTICS SYSTEMS AND METHODS

(71) Applicant: HEMEX HEALTH, INC., Portland, OR (US)

(72) Inventors: Peter Galen, Portland, OR (US); Umut Gurkan, Shaker Heights, OH (US); Arwa Fraiwan, Cleveland, OH (US); Muhammad Noman Hasan, Cleveland Heights, OH (US); Daniel E. Grupp, Portland, OR (US); Joshua King Hoyt, Portland, OR (US); James Thorne, Portland, OR (US); Brian T. Grimberg, Shaker Heights, OH (US)

(73) Assignee: HEMEX HEALTH, INC., Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/113,261

(22) Filed: Aug. 27, 2018

(65) Prior Publication Data

US 2019/0053454 A1 Feb. 21, 2019

Related U.S. Application Data

(63) Continuation of application No. 15/699,962, filed on Sep. 8, 2017, which is a continuation-in-part of application No. 15/599,368, filed on May 18, 2017.
(Continued)

(51) Int. Cl.
*A01H 5/10* (2018.01)
*A61B 5/157* (2006.01)
(Continued)

(52) U.S. Cl.
CPC ............... *A01H 5/10* (2013.01); *A01H 1/02* (2013.01); *A61B 5/15003* (2013.01);
(Continued)

(58) Field of Classification Search
CPC ........ A01H 5/10; A01H 1/02; C12N 15/8274; C12N 15/8243; C12N 15/8251;
(Continued)

(56) References Cited

U.S. PATENT DOCUMENTS 5,069,769 A 12/1991 Fujimiya et al.
5,108,754 A 4/1992 Wilburn
(Continued)

FOREIGN PATENT DOCUMENTS

JP 2002-328113 11/2002
JP 2004-069430 3/2004
(Continued)

OTHER PUBLICATIONS

Search Report and Written Opinion for Singapore Patent Application No. 112017007331.
(Continued)

*Primary Examiner* — Samuel P Siefke
(74) *Attorney, Agent, or Firm* — Lane Powell PC

(57) ABSTRACT

A point-of-care diagnostic system that includes a cartridge and a reader. The cartridge can contain a patient sample, such as a blood sample. The cartridge is inserted into the reader and the patient sample is analyzed. The reader contains various analysis systems, such as an electrophoresis detection system that uses electrophoresis testing to identify and quantify various components of the blood sample. The reader can process data from the various patient sample analysis to provide interpretative results indicative of a disorder, condition, disease and/or infection of the patient.

30 Claims, 10 Drawing Sheets

Related U.S. Application Data

(60) Provisional application No. 62/385,146, filed on Sep. 8, 2016.

(51) Int. Cl.

| | |
|---|---|
| *G01N 1/31* | (2006.01) |
| *B01L 3/00* | (2006.01) |
| *G01N 27/447* | (2006.01) |
| *A61B 5/151* | (2006.01) |
| *A61B 5/15* | (2006.01) |
| *A61B 5/00* | (2006.01) |
| *G01N 33/49* | (2006.01) |
| *A01H 1/02* | (2006.01) |
| *C12N 15/82* | (2006.01) |

(52) U.S. Cl.
CPC ............ *A61B 5/157* (2013.01); *A61B 5/1519* (2013.01); *A61B 5/15087* (2013.01); *A61B 5/15192* (2013.01); *A61B 5/150755* (2013.01); *A61B 5/7282* (2013.01); *A61B 5/742* (2013.01); *A61B 5/7405* (2013.01); *A61B 5/7475* (2013.01); *B01L 3/502* (2013.01); *B01L 3/50273* (2013.01); *C12N 15/8243* (2013.01); *C12N 15/8245* (2013.01); *C12N 15/8247* (2013.01); *C12N 15/8251* (2013.01); *C12N 15/8274* (2013.01); *C12N 15/8279* (2013.01); *C12N 15/8286* (2013.01); *C12N 15/8289* (2013.01); *G01N 1/312* (2013.01); *G01N 27/44717* (2013.01); *G01N 27/44756* (2013.01); *G01N 33/49* (2013.01); *A61B 2560/0214* (2013.01); *B01L 2300/021* (2013.01); *B01L 2300/023* (2013.01); *B01L 2300/025* (2013.01); *B01L 2300/0645* (2013.01); *B01L 2300/0672* (2013.01); *B01L 2300/087* (2013.01); *B01L 2300/0816* (2013.01); *B01L 2300/0825* (2013.01); *B01L 2300/18* (2013.01); *B01L 2400/0406* (2013.01); *B01L 2400/0421* (2013.01); *B01L 2400/0481* (2013.01); *G01N 27/44704* (2013.01); *G01N 27/44743* (2013.01); *G01N 2333/805* (2013.01)

(58) Field of Classification Search
CPC ............ C12N 15/8289; C12N 15/8286; C12N 15/8247; C12N 15/8245; C12N 15/8279; B01L 3/50273; B01L 3/502; B01L 2400/0481; B01L 2300/087; B01L 2300/0816; B01L 2300/021; B01L 2300/0825; B01L 2300/0645; B01L 2300/0672; B01L 2400/0421; B01L 2300/18; B01L 2300/023; B01L 2300/025; A61B 5/15003; A61B 5/7405; A61B 5/15087; A61B 5/15192; A61B 5/150755; A61B 5/157; A61B 5/742; A61B 5/1519; A61B 5/7475; A61B 5/7282; A61B 2560/0214; G01N 33/49; G01N 27/44717; G01N 1/312; G01N 27/44756; G01N 27/44743; G01N 27/44704; G01N 2400/0406; G01N 2333/805
See application file for complete search history.

(56) References Cited

U.S. PATENT DOCUMENTS

| | | |
|---|---|---|
| 5,202,006 A | 4/1993 | Chen |
| 5,827,681 A | 10/1998 | Krug et al. |
| 5,978,694 A | 11/1999 | Rapoport et al. |
| 6,818,185 B1 | 11/2004 | Petersen et al. |
| 7,639,359 B2 | 12/2009 | Chung et al. |
| 8,214,006 B2 | 7/2012 | Newman et al. |
| 8,423,104 B2 | 4/2013 | Wiseman et al. |
| 9,632,077 B2 | 4/2017 | Hirase et al. |
| 9,697,556 B2 | 7/2017 | Mazed et al. |
| 2001/0012612 A1 | 8/2001 | Petersen et al. |
| 2002/0012902 A1 | 1/2002 | Fuschs et al. |
| 2002/0042125 A1 | 4/2002 | Petersen et al. |
| 2002/0086416 A1 | 7/2002 | Sato et al. |
| 2004/0173456 A1 | 9/2004 | Boos et al. |
| 2004/0256230 A1 | 12/2004 | Yager et al. |
| 2005/0020893 A1 | 1/2005 | Diab |
| 2006/0013740 A1 | 1/2006 | Berndtsson et al. |
| 2006/0025659 A1 | 2/2006 | Kiguchi et al. |
| 2006/0066754 A1 | 3/2006 | Zaima |
| 2007/0059204 A1 | 3/2007 | Witty et al. |
| 2008/0227209 A1 | 9/2008 | Deng |
| 2009/0314641 A1 | 12/2009 | Rooney et al. |
| 2009/0318784 A1 | 12/2009 | Newman et al. |
| 2010/0010858 A1 | 1/2010 | Matoba |
| 2010/0147688 A1 | 6/2010 | El Hadidy |
| 2010/0149519 A1 | 6/2010 | Toofan et al. |
| 2010/0181199 A1 | 7/2010 | Sugiyama |
| 2011/0065209 A1 | 3/2011 | Heil et al. |
| 2011/0104738 A1 | 5/2011 | Forsell |
| 2011/0196222 A1 | 8/2011 | Behrend et al. |
| 2011/0244467 A1 | 10/2011 | Haswell |
| 2012/0012462 A1 | 1/2012 | Sugiyama |
| 2012/0021456 A1 | 1/2012 | Levine et al. |
| 2012/0257199 A1 | 10/2012 | Liu et al. |
| 2012/0326104 A1 | 12/2012 | Kwon et al. |
| 2014/0004501 A1 | 1/2014 | Talebpour et al. |
| 2015/0064693 A1 | 3/2015 | Khattak et al. |
| 2015/0125873 A1 | 5/2015 | Newman et al. |
| 2015/0377857 A1 | 12/2015 | Grimberg et al. |
| 2017/0108495 A1 | 4/2017 | Ikeda et al. |

FOREIGN PATENT DOCUMENTS

| | | |
|---|---|---|
| JP | 2005-538381 | 12/2005 |
| JP | 2006-064398 | 3/2006 |
| WO | WO9633410 | 7/2010 |
| WO | WO2010141921 | 12/2010 |
| WO | WO2013071301 | 5/2013 |
| WO | WO2016066754 | 5/2016 |

OTHER PUBLICATIONS

International Preliminary Report on Patentability dated Jan. 31, 2017, International Application No. PCT/US2015/042907, International filing date.
Written Opinion dated Jan. 7, 2016, International Application No. PCT/US2015/042907, International filing date.
International Search Report dated Jan. 7, 2016, International Application No. PCT/US2015/042907, International filing date.
Nov. 7, 2017 Written Opinion, International Application No. PCT/US2017/50809, International filing date Sep. 8, 2017.
International Search Report dated Nov. 7, 2017, International Application No. PCT/US2017/50809, International filing date Sep. 8, 2017.
International Search Report dated Sep. 29, 2017, International Application No. PCT/US2017/033409, International filing date May 18, 2017.
Written Opinion dated Sep. 29, 2017, International Application No. PCT/US2017/033409, International filing date May 18, 2017.
Web Page: "http://www.tedxcle.com/dr-brian-grimberg/"; Published Jan. 3, 2013; viewed Jun. 15, 2018.
Tang et al.: "Hemoglobin electrophoresis", Clinical Immunology newsletter, Elsevier, US. vol. 13, No. 8, Aug. 1, 1993.
EPO Search Report, dated Jan. 30, 2018, EPO Appl. No. 15827038.9; pp. 1-8.
Notice of Allowance dated Jun. 5, 2017, U.S. Appl. No. 15/425,729, filed Feb. 6, 2017.

(56) References Cited

OTHER PUBLICATIONS

Notice of Allowance dated Feb. 28, 2017, U.S. Appl. No. 15/425,729, filed Feb. 6, 2017.
Notice of Allowance dated Dec. 2, 2016, U.S. Appl. No. 14/766,523, filed Aug. 7, 2015.
Amendment filed Oct. 20, 2016, U.S. Appl. No. 14/766,523, filed Aug. 7, 2015.
Non-Final Rejection dated Oct. 7, 2016, U.S. Appl. No. 14/766,523, filed Aug. 7, 2015.
Notice of Allowance dated Jun. 8, 2016, U.S. Appl. No. 14/766,523, filed Aug. 7, 2015.
Preliminary Amendment filed Jan. 15, 2016, U.S. Appl. No. 14/766,523, filed Aug. 7, 2015.
International Search Report dated May 14, 2014, International Application No. PCT/US2014/015604, International filing date Feb. 10, 2014.
Written Opinion dated May 14, 2014, International Application No. PCT/US2014/015604, International filing date Feb. 10, 2014.
International Preliminary Report on Patentability dated Aug. 11, 2015, International Application No. PCT/US2014/015604, International filing date Feb. 10, 2014.
Kohn J. Separation of hemoglobins on cellulose acetate. J. Clin Pathol., Jan. 31, 1969, vol. 22, No. 1, pp. 109-111.
Graham J. L. Grunbaum B. W., A rapid method for microelectrophoresis and quantitation of hemoglobins on cellulose acetate. Am J Clin Pathol., Jun. 30, 1963, vol. 39, No. 6, pp. 567-578.
Hemechip for Early Diagnosis of Sickle Cell Disease. Jul. 1, 2014, https://contest.techbriefs.com/2014/entries/medical5025.
Protocol: Cellulose acetate electrophoresis. Sep. 17, 2013, http://web.archive.org/web/20130917003807/http://www.ithanet.eu:80/ithapedia/index.php/protocol:cellulose_acetate_electrophoresis.
Grimberg B., "Manipulations of Malaria Parasies With Magnets" p. 1-102, Jan. 27, 2012, CWRU, World Health Interest Group Meeting, Cleveland, OH.
Mens, Petra F., et al. "Laboratory evaluation on the sensitivity and specificity of a novel and rapid detection method for malaria diagnosis based on magneto-optical technology (MOT)." Malaria journal 9.1 (Published Jul. 19, 2010).
Chung et al.; Magneto-optic measurement of Brownian relaxation nanoparticles; Journal of Magnetism and Magnetic Materials 320; 2008, pp. 91-95.
Jan. 30, 2017 Preliminary Amendment dated Jan. 30, 2017, U.S. Appl. No. 15/500,447, filed Jan. 30, 2017.
May 19, 2018 Notice of Allowance, U.S. Appl. No. 15/699,962, filed Sep. 8, 2017.
Feb. 7, 2018 Amendment, U.S. Appl. No. 15/699,962, filed Sep. 8, 2017.
Sep. 27, 2017 Office Action, U.S. Appl. No. 15/599,368, filed May 18, 2017.
Dec. 27, 2017 Amendment, U.S. Appl. No. 15/599,368, filed May 18, 2017.
Jan. 8, 2018 Final Office Action, U.S. Appl. No. 15/599,368, filed May 18, 2017.
May 9, 2018 Amendment, U.S. Appl. No. 15/599,368, filed May 18, 2017.
International Preliminary Report on Patentability dated Mar. 12, 2019, International Application No. PCT/US2017/50809, International filing date Sep. 8, 2017.
International Preliminary Report on Patentability dated Mar. 12, 2019, International Application No. PCT/US2017/033409, International filing date May 18, 2017.
Old et al. (Chapter 3 of Prevention of Thalassaemias and Other Haemoglobin Disorders: vol. 2: Laboratory Protocols, 2nd edition, Haemoglobin pattern analysis) (Year: 2012).
Office Action for Japanese Patent Application No: 2017-505197, dated Jan. 22, 2019.
NonFinal Office Action mailed, U.S. Appl. No. 15/500,447, filed Jan. 30, 2017.
Office Action for Chinese Patent Application No.: 201580052224.X, dated Nov. 22, 2018.
Jun. 3, 2019, Advisory Action, U.S. Appl. No. 15/500,447, filed Jan. 30, 2017.
Jun. 4. 2019, Amendment, U.S. Appl. No. 15/500,447, filed Jan. 30, 2017.
First Examination Report dated Jun. 4, 2019, Indian Application No. 201917013514, filed Apr. 3, 2019.
First Examination Report dated May 31, 2019, Indian Application No. 2019017013517.

DIAGNOSTICS SYSTEMS AND METHODS

CROSS-REFERENCE TO RELATED APPLICATIONS

This application is a continuation of Ser. No. 15/699,962, filed Sep. 8, 2017, which is a continuation-in-part of pending U.S. patent application Ser. No. 15/599,368, filed May 18, 2017, which claims the benefit of U.S. Provisional Patent Application Ser. No. 62/385,146, filed Sep. 8, 2016, the contents of which are herein incorporated by reference in their entirety This application also claims the benefit of U.S. Provisional Patent Application Ser. No. 62/385,146, filed Sep. 8, 2016, the contents of which are herein incorporated by reference in their entirety.

This application is related to International Patent Application PCT/US2017/033409, filed May 18, 2017, the contents of which are herein incorporated by reference in their entirety.

BACKGROUND

Patient diagnostic services save lives, reduce the time to treatment for the patient and provide valuable insight for targeted treatment. In many developed countries, modern medical facilities can provide patients with the most advanced diagnostic services allowing patients to be efficiently and effectively treated. In less developed countries or regions, high quality medical facilities and diagnostic services can be lacking, often due to economic and infrastructure considerations. In many less developed countries, the economy cannot afford the latest in medical technology and infrastructure, such as a robust power grid or highly trained clinicians, required to support the high demands of modern medical technology. Sadly, a large portion of the world's population resides in underserved or developed areas where the lack of efficient and effective diagnostic services critically impacts the population morbidity, mortality and overall health. This lack of medical care can lead or contribute to knock-on effects, such as low economic and educational development.

Often, many less developed countries and areas also lack sufficient trained users that are typically required to perform the necessary diagnostic services. This can lead to inconclusive or erroneous results from diagnostic services or to significant delays in diagnosis as the diagnostic services are required to be performed in another location that has the requisite infrastructure and/or knowledge to perform the diagnostic service. For patients, this can mean further delays in treatment, which can decrease their chances of survival, increase the spread of the disease, and/or lead to increased debilitation caused by the disease or condition.

Where large laboratories may be prohibitively expensive and difficult to staff, point-of-care diagnostic devices may provide an effective solution. Such a solution could provide timely, accurate, and cost-effective health care.

One of the treatable common ailments effecting less developed countries are hemoglobin disorders, such as sickle cell disease (SCD), thalassemia and other hemoglobinopathies. These are genetic disorders that are believed to have evolved in response to malaria. With population migration, these conditions have spread to the global population and affect the livelihood and health of a large number of people. With early detection or diagnosis, these conditions can be treated and managed before they have significant adverse impact on the stricken individual. As with malaria, these disorders affect the populations of less developed countries and areas, which have limited to no access to the diagnostic services to rapidly, effectively and efficiently diagnose the conditions.

A further challenge is unreliable power sources in less developed areas. Thus it would be desirable to have diagnostic solutions that are of low enough power consumption to be able to run on batteries.

Yet a further challenge is a point-of-care device is subject to varying conditions of the environment, the patient sample, and disposable elements of the device itself. This may yield wide variation in test results. Thus it is desirable to have a diagnostic device that is either insensitive to such variations or is self-calibrating.

What is needed is a diagnostic device or service for the diagnosis of biologic fluid disease, conditions or ailments that is point-of-care, in vitro, low-cost, rapid, accurate, self-calibrating, and capable of evaluating data and producing a diagnosis without the aid of a skilled clinician. Such a device would greatly benefit many countries and areas, especially those that are less developed.

DETAILED DESCRIPTION

It shall be noted that, as used in the specification and the appended claims, the singular forms "a," "an" and "the" include plural referents unless otherwise specified. Additionally, the use of the words "and" and "or" may be interpreted to be used interchangeably and to generally also encompass "and/or."

Various example point-of-care, in vitro diagnostic devices and methods for detecting and helping to diagnose blood disorders, and specifically inherited blood disorders and/or other conditions/diseases, are described herein. The disclosed diagnostic devices include a cartridge and a reader that interface to analyze a patient biologic sample, such as a blood sample, to provide a diagnosis, or data regarding one or more disorders, diseases, or conditions of the patient. The cartridge can contain or support the biologic sample for analysis by one or more diagnostic systems of the reader. An electrophoresis system, and/or further in vitro diagnostic and/or patient biologic sample analysis systems, such as a magneto-optical system, can be included in the reader and cartridge to diagnose and/or provide patient biologic sample data regarding a variety of diseases or conditions. The cartridge and reader provide an economic, efficient, and effective point-of-care diagnostic system. The biologic sample could be the patient's blood, saliva, urine, other fluid, a liquid suspension of tissue, a combination of fluids or other biologic component. Several of the examples discussed herein explain the systems and methods of analyzing a patient blood sample, but it is understood that any biologic sample could be used. Additionally, the electrophoresis systems described herein can also be used to analyze other, non-biologic, liquids and/or compounds using the electrophoresis analysis method.

Figure 1:
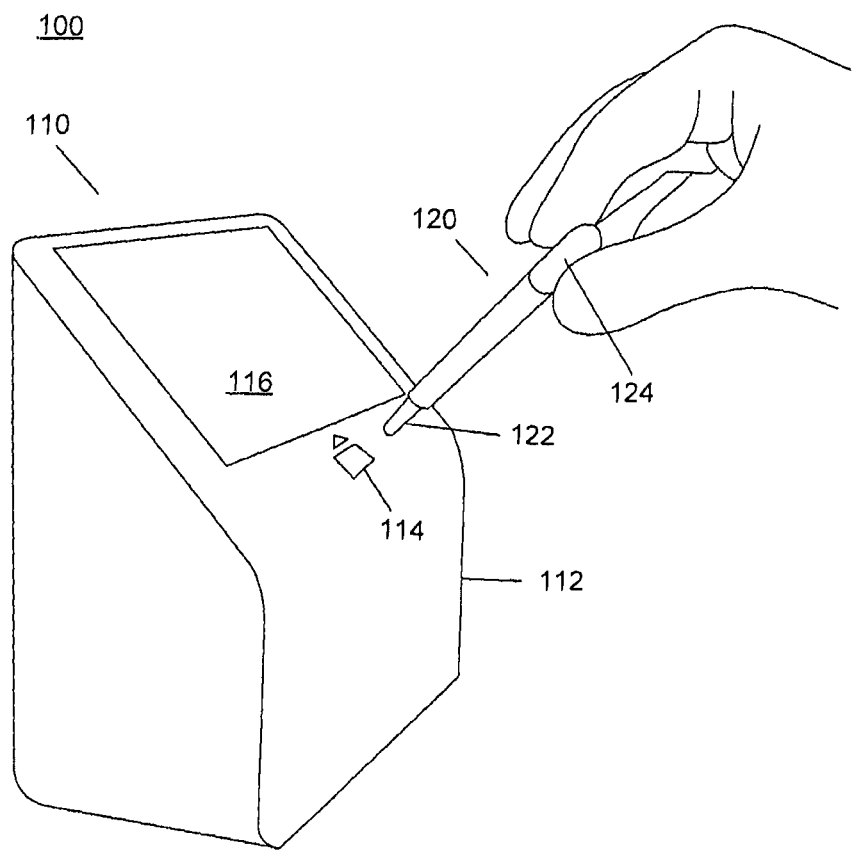
FIG. 1 illustrates an example diagnostic system.

FIG. 1 illustrates an example reader 110 and cartridge 120 of a point-of-care blood diagnostic system 100. A point-of-care blood diagnostic system includes devices that are physically located at the site at which patients are tested and sometimes treated to provide quick results and highly effective treatment. Point-of-care devices can provide information and help in diagnosing patient disorders and/or infections while the patient is present with potentially immediate referral and/or treatment. Unlike gold standard laboratory-based blood testing for disorders and/or infections, the disclosed point-of-care devices enable diagnosis close to the patient while maintaining high sensitivity and accuracy aiding efficient and effective early treatment of the disorder and/or infection.

The reader 110 includes a housing 112, a cartridge receptacle 114 and a display 116. The cartridge 120, which contains the patient sample and, optionally dilutants, markers, reagents and/or materials, is inserted into the cartridge receptacle 114 of the reader 110 to transfer the patient sample, treated or untreated, into the reader 110 to perform a diagnostic test or analysis. The cartridge 120 more generally is placed in proximity to the reader in such a manner that the reader can interact with one or more elements of the cartridge to perform analysis of the patient sample. The cartridge 120 can include a pipette-like end 122 and a bulb 124 for siphoning a patient sample into the cartridge 120 in preparation for the diagnostic test. Alternatively, the cartridge 120 can include a capillary tube by which the patient sample can be obtained for analysis and/or testing. In a further embodiment, collection of the patient blood sample can be performed using blotting paper that is included in the cartridge 120 to collect a blood spot that can be analyzed by the point-of-care blood diagnostic system 100.

The housing 112 of the reader 110 can be constructed of materials such as plastic or metal and is preferably sealed with a smooth surface, which allows the reader 110 to be easily cleaned and/or disinfected and resist external water and or dust. Further, the housing 112 is sufficiently strong to allow the safe transport and use of the reader 110 without substantial damage to the reader 110 and the diagnostic systems within. Additionally, the housing 112 can have properties, that shield or minimize the exposure of the interior of the reader 110 to temperature and/or humidity variations and/or light intrusion. The robustness of the reader 110 allows it to be used in a variety of locations and environments without adversely affecting the results of the diagnostic system.

The housing 112 of the reader 110 can also include vibration isolation to prevent vibration of the reader 110 during the measurement process to assist with preventing analysis error of the patient sample. Vibration isolation can include suspending and/or isolating the components and/or systems of the reader 110 within the housing 112 or containing the components and/or systems within an internal housing that is suspended and/or isolated from the external housing 112. Alternative vibration isolation can include anti-vibration feet or mounts on which the reader 110 can sit on a surface. Additional vibration isolation can include placing the reader 110 on a cushioned and/or anti-vibration mat to reduce or limit the vibration and/or disturbance of the reader 110 by its external environment.

The cartridge receptacle 114 can be conformably shaped to receive the cartridge 120. The cartridge 120 can be received partially or completely into the cartridge receptacle 114 or the reader 110. Alternatively, the cartridge 120 can be otherwise connected, such as by an external receptacle or conduit, to the reader 110 to transfer the patient sample, or portion thereof, into the reader 110. Such an external receptacle or conduit can be electrically coupled to the electronics housed in the reader 110 by a wireless or hard-wire connection of any suitable configuration.

Figure 2A:
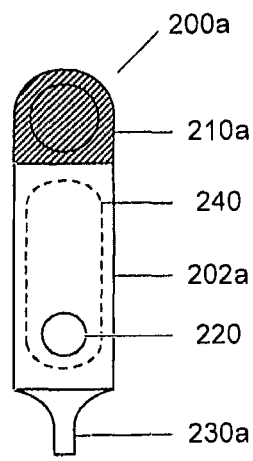
FIGS. 2A-2B illustrate example cartridges.
Figure 2B:
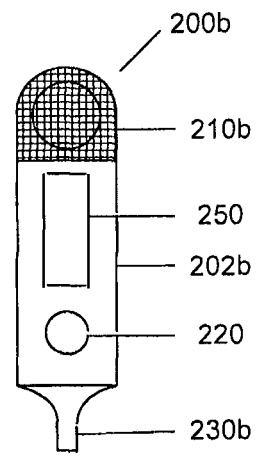

FIGS. 2A-2B illustrate example cartridges 200a and 200b. Each of the example cartridges 200a, 200b include a housing 202a, 202b an upper portion 210a, 210b and a lower portion 230a, 230b. The cartridges 200a, 200b can include a sample chamber, such as 240 of FIG. 2A, that is internal to the cartridge 200a, 200b and can store a patient sample, such as a blood sample, within the cartridge 200a, 200b. The cartridges 200a, 200b transport or store a patient sample for analysis, or reading, by a reader. Further, the cartridges 200a, 200b can interface with the reader to assist with or facilitate the reading or analysis of the patient sample stored within the cartridge 200a, 200b. That is, the cartridge 200a, 200b can include features, such as an optical window 220 and an electrophoresis element 250 of cartridge 200b of FIG. 2B to assist with the analysis of the patient sample within the cartridge 200a, 200b. The cartridge 200a, 200b can also transfer all or a portion of the patient sample to the reader for analysis of the patient sample. The patient sample, or portion thereof, from the cartridge 200a, 200b can be transferred to a blood sample chamber of the reader or to another location of the reader, or external from the reader, for analysis of the patient blood sample.

The cartridges 200a, 200b can be condition, disease and/or ailment specific or multiple condition, disease and/or ailment specific. The cartridges 200a, 200b can include various features, external and/or internal, that customize a particular cartridge for the analysis of a specific, singular or multiple, condition, disease and/or ailment. The cartridge specificity can include the patient sample size volume of the cartridge, various dilutants, markers and/or reagents in the cartridge, the interface of the cartridge with the reader and other design and/or construction specification of the cartridge in relation to one or more particular conditions, diseases and/or ailments.

The housing 202a, 202b of the cartridge 200a, 200b can include structural, material and/or geometric features that assist or facilitate the analysis and/or acquisition of the patient sample. Such features can include internal chambers, such as the sample chamber 240 of FIG. 2A, to store the patient sample or other fluids or compounds, that are sized to ensure adequate sample size for the analysis of the collected patient blood sample, interfaces that interact with, engage, or facilitate the systems of the reader during analysis of the patient sample. Other features can include environmental controls that maintain the collected patient sample in a suitable condition for analysis, and other features and/or considerations. For example, an internal chamber of the reader could manually or automatically interface with the inserted cartridge via a port to cause dilutants, markers and/or other chemical treatments to mix with the patient sample in the cartridge. Such a port would be a passage, like a tube, that connects the sample chamber of the cartridge with the port so fluids can be added to the cartridge. The addition of such external fluids can be triggered manually when a user actuates a switch or other actuator, which the user may do in response to a user prompt to do so. The cartridge housing 202a, 202b can be formed of a suitable material such as a plastic, composite and/or metal to create a robust, disposable cartridge 200a, 200b. Additionally, the housing 202a, 202b material can be selected for the ability to be sterilized, such as sterilizing the cartridge 200a, 200b prior to use, for reuse or for killing pathogens prior to disposal.

Environmental considerations can also be used in the determination of a suitable material(s) for the cartridge housing 202a, 202b. Such environmental considerations can include the biodegradability of the housing material, the recyclability of the housing material, the incineration by-products of the housing material and other environmental considerations. These environmental considerations can reduce the environmental impact of the disposal, recycling and/or reuse of the cartridges 200a, 200b after use.

The housing 202a, 202b of the cartridge 200a, 200b can include a patient identification marker or an area to apply or mark patient identification onto the cartridge 200a, 200b. This marker could be in machine readable or human readable form or both. The patient identification allows the correlation of the analysis of the collected patient sample with a particular patient. Additionally, the reader can detect the patient identification marker to correlate the analysis with a patient, including automatically appending the analysis results to a patient's medical records. In an example embodiment, the patient identification can be obfuscated to remove patient personal information, such as a name, from the cartridge 200a, 200b, instead the patient can be assigned a random number, or sequence of characters, that is correlated to the particular patient in the reader, a computer or other system.

Patient diagnostic and demographic information can also be used for analysis to determine trends or emergence of conditions, disorders, diseases and/or ailments. This analysis can be used to prevent or minimize the spread of the condition/disorder and/or targeted diagnosis and/or treatment of the condition/disorder. For various conditions once properly diagnosed, such as a sickle cell and other hemoglobin conditions, geographical correlation of the prevalence of the condition can be used to perform measures to mitigate and minimize the effects of the condition on the target population.

The upper portion 210a, 210b of the cartridge 200a, 200b can include identification marker(s), such as a color, pattern, name, or other distinguishing features. The identification marker can be used to indicate the use of the cartridge 200a, 200b for the analysis of a specific condition(s), disease(s), and/or ailment(s). This can provide a clear, visual indication to a user that the cartridge 200a, 200b is to be used with specific analysis or analyses.

Additionally, the upper portion 210a, 210b can be a portion of a sample collection element, such as a suction bulb, actuation element, or capillary tube to assist or facilitate the collection of the patient sample into the cartridge 200a, 200b. As a suction bulb, the upper portion can be formed of a resilient or flexible material capable of deforming in volume to assist in the uptake of a patient sample within the cartridge 200a, 200b. As an actuation element, the application of pressure or other input by a user, other or device to the upper portion 210a, 210b of the cartridge 200a, 200b can actuate the passive or active acquisition of a patient sample into the cartridge 200a, 200b in preparation for analysis, such as extending and/or retracting a needle or capillary tube. A capillary tube is one means of passively collecting the sample with no user or machine pressure required.

Further, the upper portion 210a, 210b can contain a dilutant, marker, reagent or other fluid or substance that is stored internally in a chamber and that can be released into and/or mixed with the patient sample within the cartridge 200a, 200b. Application of pressure to the upper portion 210a, 210b of the cartridge 200a, 200b can introduce the contained substance or fluid into the patient sample within the cartridge 200a, 200b which mixes the patient sample with the contained substance(s) or fluid(s). Example dilutant ratios can include from 1:0.5 to 1:100. The contained substance or fluid can assist with the analysis of the patient sample, preparation of the patient sample for analysis, preservation of the sample for analysis or other desirable or necessary patient sample modification for efficient and effective analysis of the patient sample.

Additionally, the upper portion 210a, 210b of the cartridge 200a, 200b can be contoured and/or shaped to provide a comfortable, ergonomic, and/or easy grip for a user to handle the cartridge 200a, 200b during insertion and/or extraction into/from the reader or diagnostic device. Alternatively, the surface texture of the upper portion 210a, 210b can be such that it improves the ability of a user to grip the cartridge 200a, 200b.

The optical window 220 can be included on the cartridge 200a, 200b, which allows light to pass into and/or through a portion of the cartridge 200a, 200b such as a sample chamber containing the patient sample, such as 240 of FIG. 2A. The ability to pass light into and/or through the sample volume within the cartridge 200a, 200b can be a necessary step during analysis of the patient sample within the cartridge 200a, 200b. The optical window 220 can be a material and/or construction that necessarily or desirably alters light entering the optical window 220 as a part of the analysis of the patient sample within, such as collimating, filtering, and/or polarizing the light that passes through the optical window 220. Alternatively, the optical window 220 can be transparent or translucent, or can be an opening within the housing 202a, 202b of the cartridge 200a, 200b. The cartridge 200a, 200b can include a reflector opposite the optical window 220, 220b that reflects the incoming light back through the optical window 220a, 220b or through another optical window, or can include a further optical window opposite the light entry window to allow light to pass through the cartridge 200a, 200b.

An electrophoresis element, such as 250 of cartridge 200b of FIG. 2B, can assist with performing an electrophoresis analysis of a patient sample within the cartridge 250. The electrophoresis element 250 can include electrodes to establish an electrical gradient across the element to perform the electrophoresis analysis. A cover can be included to protect the electrophoresis element, while still allowing the results to be viewed either through the cover or by removal of the cover. The cover can be optically transparent to allow optical viewing of the results and/or the electrophoresis process being performed. Light can be reflected off of and/or transmitted through the electrophoresis element 250 to assist with viewing the results displayed thereon. The cartridge 200b can include one or more structural features to facilitate the transmission of light through the electrophoresis element 250.

The lower portion 230a, 230b can house or be a portion of the sample collection system. In the examples shown in FIGS. 2A and 2B, the lower portion 230a, 230b can include a channel or tube through which the patient sample can be transferred into the interior of the cartridge 200a, 200b. The lower portion 230a, 230b can also house a portion of the sample collection system, such as an extendable needle like a lancet or a capillary tube through which the patient sample can be transferred to the interior of the cartridge 200a, 200b.

The lower portion 230a, 230b can also include elements and/or systems to assist with the analyzing and/or storage of the patient sample. This can include an interface and/or mechanism to release at least a portion of the patient sample from within the cartridge 200a, 200b into the reader and/or a barrier or seal that restrains and/or preserves the patient sample within the cartridge 200a, 200b.

The lower portion 230a, 230b can further include an indicator that is visible once the cartridge 200a, 200b has been previously used. This can prevent cross-contamination of patient specimens and/or prevent the reuse of a single-use cartridge 200a, 200b which could alter or otherwise compromise the results of the patient sample analysis. The indication can be structural in nature, with an alteration, such as a removal or break in a portion of the cartridge 200a, 200b housing 202a, 202b of the lower portion 230a, 230b that is a visible once the cartridge 200a, 200b has been used or has acquired a patient sample. Additionally, the lower portion 230a, 230b can deform after acquisition of a patient sample within the cartridge 200a, 200b, which prevents further collection of a patient sample(s) using the cartridge 200a, 200b. The indication could be electrical.

Figure 3A:
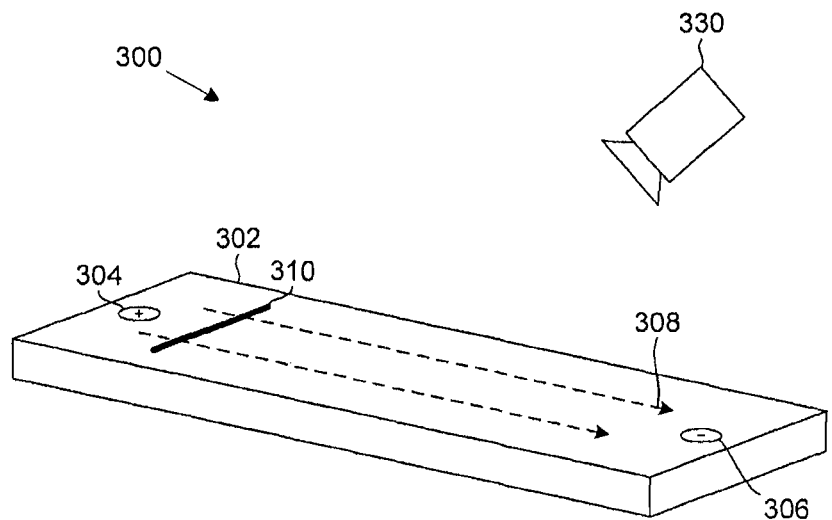
FIGS. 3A-3B illustrate an example electrophoresis detection system.
Figure 3B:
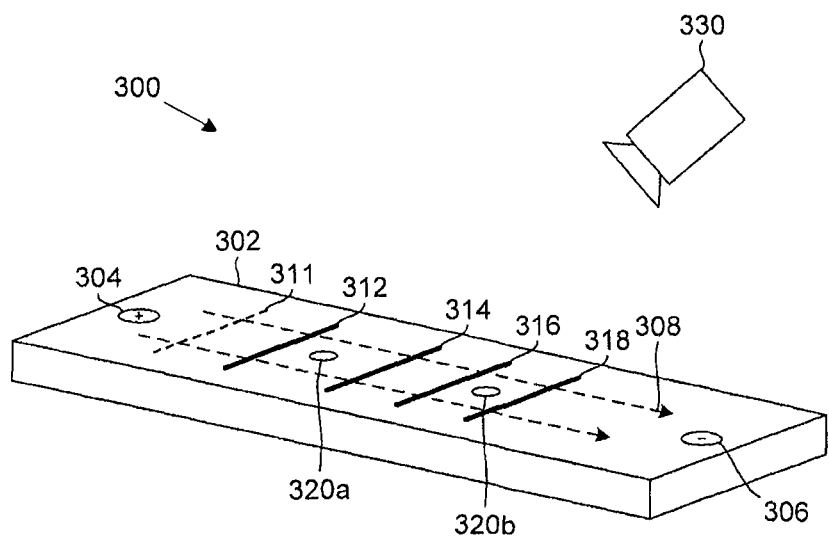

FIGS. 3A-3B illustrate an example electrophoresis detection system 300. The electrophoresis detection system 300 includes an electrophoresis strip 302, electrodes 304, 306, patient sample 310 and an optical imaging device 330. The electrophoresis analysis of a patient sample 310 can be used to evaluate aspects of the patient sample 310 that are effected due to an applied electric potential or voltage. Aspects of the patient sample 310 that can be affected by an electric potential can include hemoglobin, due to its charge. Various hemoglobin disorders can be diagnosed, evaluated and/or monitored using the electrophoresis testing, including determining the relative proportions of the hemoglobin types of the patient sample 310. Results of the electrophoresis analysis can be optically captured by imaging. A light source, not shown, can be used to assist the capture of the results, with the light source emitting light that is then reflected and/or transmitted through the electrophoresis strip 302 to assist with imaging and/or visualizing the electrophoresis results thereon.

FIG. 3A illustrates the initial set-up of the electrophoresis process. The electrophoresis strip 302 can have a buffer solution deposited thereon to assist with establishing the electrical conductivity between the two electrodes 304 and 306. A patient sample 310, such as a blood sample, is placed on the electrophoresis strip 302 in a controlled manner. In the example shown in FIG. 3A, the patient sample 310 is shown deposited as a line, the more precise and/or controlled the sample is deposited onto the electrophoresis strip 302 the more clearly the banding can be visualized. Additionally, the patient sample 310 can include added compounds/components, such as one or more markers. The added compounds/components can assist with the electrophoresis process and/or assist with interpreting the electrophoresis results.

For example, the one or more markers can have known migrations rates and/or distances for a given applied voltage and/or voltage application time. Alternatively, these markers can normalize the results of the electrophoresis process by having migration rates relative to the sample, thereby reducing the effects of sample-to-sample variability. These markers can assist with evaluating the resultant banding of the patient sample 310. With the patient sample 310 in place, a voltage is applied using the electrodes 304 and 306, causing various components of the patient sample 310 to migrate across the electrophoresis strip in the direction indicated by arrow 308 over a defined time. The various components of the patient sample 310 will separate into bands due to the applied voltage and the physical and electrical properties of the various components. One or all of the applied voltage, current and the application time can be predetermined or preset based on the various parameters of the electrophoresis testing being performed. Alternatively, one or more of the voltage, current and application times can be variable and based on the banding of the patient sample or an added compound/component therein. For example, the movement of a marker added to the patient sample 310 can be monitored as the marker moves across the electrophoresis strip 310. That is, imaging/monitoring of the electrophoresis testing, and/or the markers thereon, can be performed in a continuous or timed interval manner during the testing process. For example, images of the electrophoresis process can be continuously captured, such as by a video imaging process, or the images can be captured at regular intervals based on time and/or the distance one or more bands have traveled. Once the marker has reached a predetermined location across the electrophoresis strip 302, the test can be terminated with the removal of the applied voltage.

FIG. 3B illustrates the completed electrophoresis process. After applying a voltage, via electrodes 304 and 306, for an amount of time, the patient sample 310 has separated into the various bands, 312, 314, 316 and 318, which have moved from an initial patient sample location 311. Additionally, added markers 320a and 320b have separated from the initial patient sample 310 and have moved along the length of the electrophoresis strip 302. The intensity, location and/or other band detection characteristics of the various bands 312, 314, 316 and 318 can be used to identify the components, and their relative proportions, of the initial patient sample 310. The optical imaging device 330 can image the electrophoresis strip 302, during and/or after the electrophoresis process, for processing to identify the compounds represented by the various bands 312, 314, 316 and 318 and their relative proportions.

The electrophoresis detection system 300 can be used to identify and monitor hemoglobin disorders, such as sickle cell disease (SCD) and thalassemia. For SCD, monitoring the various hemoglobin types and their proportions is an important part of patient treatment. SCD patients produce sickle hemoglobin (HbS), resulting in malformed red blood cells that have reduced oxygen carrying capacity and present other patient issues due to their malformed shape and properties. The treatment for SCD patients is often blood transfusions, which increases the proportion of normal adult hemoglobin (HbA) for the patient and hydroxyurea which stimulates the formation of fetal hemoglobin (HbF). A patient's hemoglobin levels can be monitored to determine the efficacy of the treatment regime and to properly time the administration of various therapies. Using the disclosed electrophoresis systems and methods disclosed herein, levels of the various hemoglobin types of a patient can be monitored to more accurately and effectively treat hemoglobin disorders.

Figure 4:
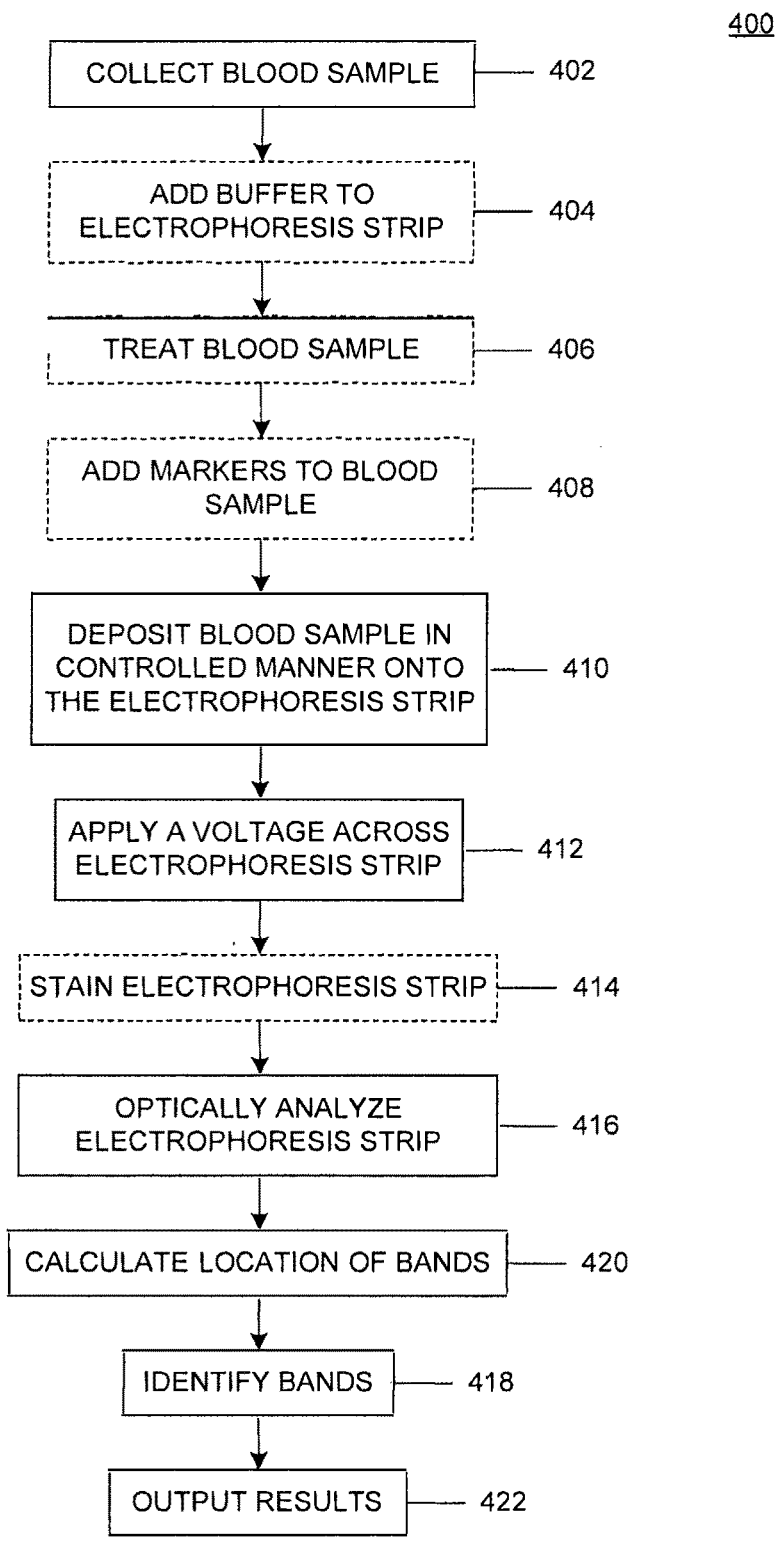
FIG. 4 illustrates an example disease and/or condition analysis method using the example electrophoresis detection system shown in FIGS. 3A-3B.

FIG. 4 is an example analysis method 400 The analysis of a patient sample, which is patient blood in this example, is performed to determine a blood characteristic, which can include the presence of a disease or condition, quantification of a disease or condition, likelihood of the presence of a disease or condition, a characteristic that can be indicative of a disease or condition, a quantification of a characteristic that can be indicative of a disease or condition, and/or other blood characteristic that can be effected by the presence of a disease or condition of the patient. The example method of FIG. 4 can be performed using a reader and cartridge system, such as the example shown in FIG. 1. The reader can include one or more systems and/or elements to analyze, quantify, identify and/or otherwise determine characteristics of a patient sample that can be indicative of the presence of a disease and/or condition of the patient.

An initial step 402 of the method 400 can include the collection of a patient sample for analysis, in this example, a blood sample. Alternative and/or further patient samples, such as saliva, tissue and/or other bodily fluids and also non-biological samples can be collected for analysis by one or more systems of the reader.

At 404, a buffer can be added to the electrophoresis strip in preparation for the electrophoresis testing of the collected blood sample. The buffer can be a liquid that wets the electrophoresis strip and can contain salts or other compounds to assist with the application of a current across the electrophoresis strip. The buffer can be stored within the cartridge or the reader and applied by the cartridge or reader in response to starting an electrophoresis testing process, such as by a user, the reader and/or the cartridge. Alternatively, the electrophoresis strip can have the buffer pre-applied during a manufacturing or other process. In a further embodiment, the electrophoresis strip can include one or more components of the buffer that are applied to the electrophoresis strip in a dry state, such as during a manufacturing process, and a fluid, such as deionized water, can be applied to the electrophoresis strip prior to use to hydrate the dry state components and wet the electrophoresis strip with the buffer solution.

The collected blood sample 402 can then be treated, if necessary or desired, for analysis. The treatment of the blood sample can include diluting the blood sample, which can be done by mixing the collected blood sample with a dilutant, such as deionized water or other fluid that dilutes the blood sample. The dilutant can alter the viscosity of the blood sample, the opacity or translucence of the blood sample, or otherwise prepare the blood sample for analysis using the reader. Preferably, the dilutant does not impact the resulting analysis of the blood sample and/or assists with preparing the blood sample for analysis. This can include lysing the cells of the blood sample to release the various cellular components for electrophoresis analysis by the reader. Lysing agents can include fluids, such as water or various chemicals, and powders. Additionally, mechanical lysing can be used, such as by sonication, maceration and/or filtering, to achieve adequate lysing of the cells of the blood sample in preparation for analysis of the sample.

At 408, one or more markers can be added to the blood sample. The added markers can assist with visualizing the completed electrophoresis results. For example, a marker that moves at the same relative rate as a hemoglobin type due at a predetermined applied voltage can be added. The marker will move with the hemoglobin type containing portion of the blood sample across the electrophoresis strip in response to the applied voltage. The marker can have a color, or other optical properties that makes visualizing the marker easier. Since the marker moves with the relative to a specific hemoglobin type, the easier to visualize marker can make it easier to determine the distance the hemoglobin type has moved across the electrophoresis strip in response to the applied voltage.

At 410 the blood sample can be deposited onto the electrophoresis strip in a controlled manner, preferably applied in a "line" perpendicular to the length of the electrophoresis strip. The controlled manner of deposition can include controlling the amount of blood sample deposited, the area across which the blood sample is deposited, the shape of the area across which the blood sample is deposited and/or other deposition characteristics. One or more systems and/or components of the reader and/or cartridge can be used to deposit the blood sample in the controlled manner onto the electrophoresis strip.

Alternatively, the process 402 of collecting the blood sample can be combined with the deposition of the blood sample 410 into a single step. The patient blood sample can be directly deposited, such as from a fingerstick, onto a region of the electrophoresis strip for analysis.

With the blood sample deposited onto the electrophoresis strip, a voltage can be applied across the electrophoresis strip at 412 to cause the separation of the blood sample into various bands of components. The voltage or current can be applied at a predetermined level or series of levels and for an amount of time. As discussed previously, the application time of the voltage can be predetermined or based on the movement of one or more bands of the patient sample, measurement of an electrical parameter such as resistance or an added compound/component. A higher applied voltage can cause the bands to move across the electrophoresis strip at a greater speed, however, the band shape can be distorted making the interpretation of the banding difficult. A lower applied voltage can increase band fidelity but can take a longer time to perform the requisite testing. The applied voltage can be selected to optimize testing efficiency while maintaining a desired or minimum fidelity level. Further, the applied voltage can be varied during testing, such as applying a higher voltage initially and then applying a lower voltage. The varied application of the voltage can cause the initial band separation and movement and the later applied lower voltage can assist with increasing the fidelity of the resultant banding pattern. Additionally, varying voltages and/or currents can be applied during the electrophoresis process in response to a measurement of the bands formed by the blood and/or the band or bands formed by the markers in a predetermined ratio, to maintain a constant rate of travel of the marker band or a portion thereof.

Additionally, environmental conditions within the reader and/or cartridge can be controlled during the electrophoresis process. Control of the environmental conditions can be done to maintain a stable environment in which the electrophoresis process is performed in order to minimize potential error and variance that can be caused due to environmental fluctuations. For example, a heat sink can be thermally connected to the electrophoresis strip, the cartridge and/or the reader, or portions thereof, to limit the temperature of the electrophoresis strip during testing to improve or maintain the quality of the results.

After completion of the electrophoresis process, the electrophoresis strip can be optionally stained at 414. Staining the electrophoresis strip and the bands thereon can assist with the analysis and/or evaluation of the banding. For example, a stain for hemoglobin can be used to stain the bands to assist with determining a position of the bands across the electrophoresis strip. The cartridge and/or reader can include the stain and the required systems/components for applying the stain to the electrophoresis strip. Alternatively, a user can stain the electrophoresis strip before band analysis. Alternatively or in addition, a short high voltage can be applied at the end of the test essentially burning the hemoglobin bands and making them visually persistent. The high voltage may also reduce the risk of viable pathogens.

At 416, the electrophoresis strip can be optically analyzed, including imaging the electrophoresis strip and the bands thereon. The electrophoresis strip can be imaged using one or more light sources emitting one or more spectrums of light. Multiple images of the electrophoresis strip can be captured in various lighting conditions in order to assist with analyzing/evaluating the bands. The image capture can be accomplished using one or more imaging sensors, such as a digital imaging sensor and can be performed throughout the testing process or at the conclusion of the test. The captured image(s) can be processed to evaluate and/or analyze the electrophoresis test results.

At 418, the final location of the bands can be calculated. The calculation can determine the distance each of the bands traveled, due to the applied voltage during testing, from the initial blood sample placement on the electrophoresis strip. Along with the distance of travel, a speed of travel of each band can be calculated based on the elapsed voltage application time and the distance traveled. Using the identity and location of each of the bands, the various components/compounds of the initial blood sample, and their proportions, can be determined. For a hemoglobin disorder test, this can include identifying the various hemoglobin types (HbS, HbA, HbF) present in the blood sample and the proportions of each.

As part of the analysis of the electrophoresis tests, the bands formed during the testing can be identified at 420. Identification of the bands can include associating one or more compounds/components of the initial blood sample with each of the bands of the electrophoresis. For example, identifying the bands can include associating each of the bands with a hemoglobin type. The identification of the bands can be assisted by markers that were previously added to the blood sample prior to the electrophoresis testing. The markers can be selected so that their final position along the electrophoresis test aligns with one or more of the compounds/components of interest in the blood sample. Alternatively, the marker can be selected to be interspersed between two bands so assist with differentiating the bands for identification.

Once the analysis of the blood sample is complete, the results can be output 422. The output of the results can include the identified blood characteristic(s), which can include a disorder, condition, disease and/or ailment, the identification of the compounds/components of the blood sample and relative proportions of each of the identified compounds/components. For example, the results can include the identification of the various hemoglobin types present in the initial blood sample and the proportions of each hemoglobin type. The output can be displayed or relayed to the user in a visual output, such as on a display, auditory such as by a speaker, or other manner. This can include transmitting the output results to an external device, such as a computer, through a wired or wireless connection or communication protocol, such as by a Bluetooth® connection.

Figure 5:
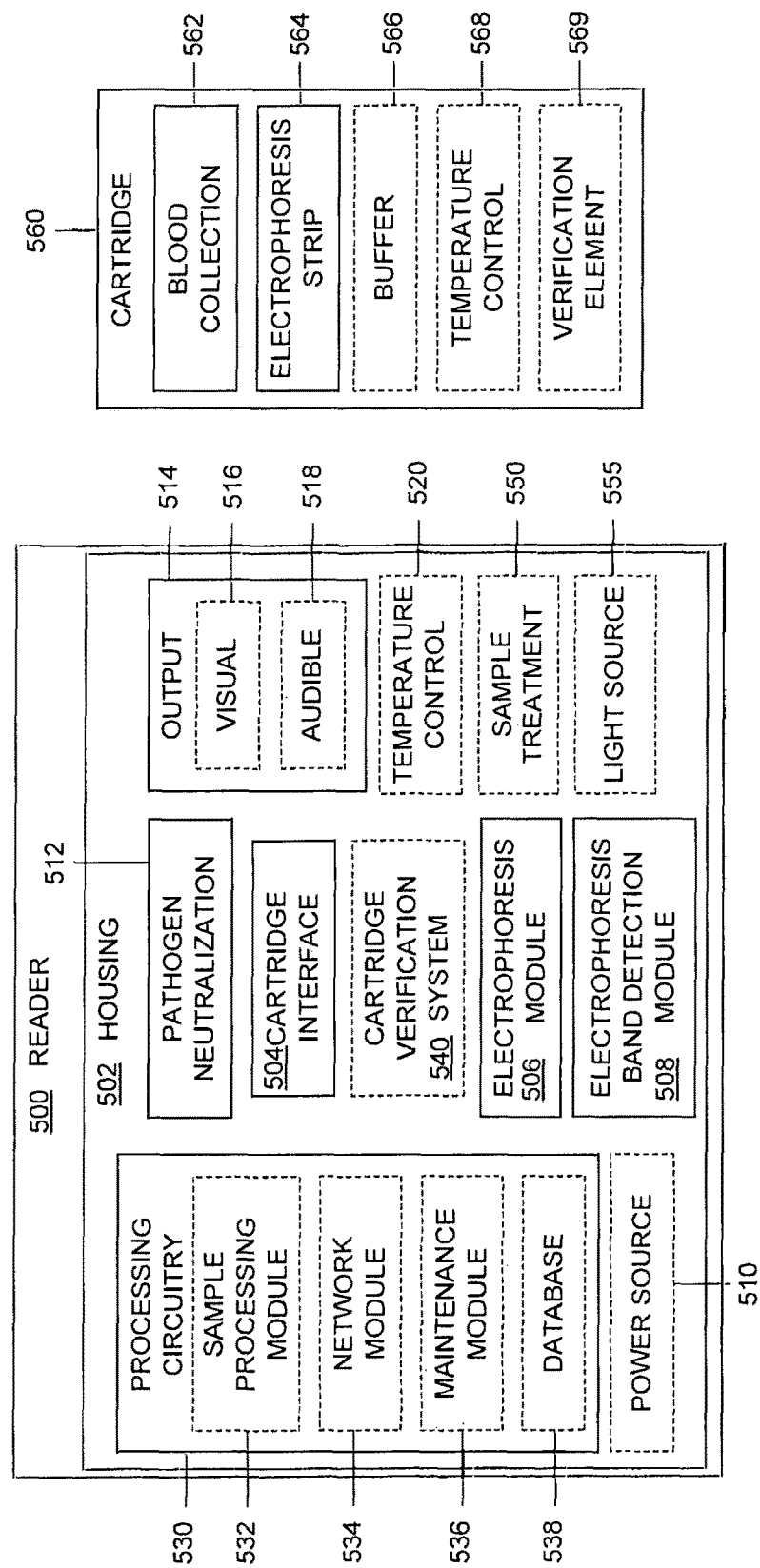
FIG. 5 is a block diagram of an example diagnostic system.

FIG. 5 illustrates an example reader 500 and a cartridge 560. The reader 500 can include all or a portion of the required systems and/or elements required to perform analysis of a patient sample. The cartridge 560 can include none or a portion of the systems and/or elements required to perform analysis of the patient sample. The reader 500 and cartridge 560 interface to perform the analysis, such as the method 400 of FIG. 4, of a patient sample.

The reader 500 includes a housing 502 that surrounds and encloses some portion or all of the reader components. FIG. 5 shows that the housing encloses all components of the reader 500, however, one of skill in the art will appreciate that any one or more components can be external to the housing, as needed or desired. As previously discussed, the housing 502 of the reader 500 is constructed of suitable materials which may involve a suitably robust construction such that the reader 500 is rugged and portable. Alternatively, the reader 500 can be designed and/or constructed for use in a permanent or semi-permanent location, such as in a clinic or laboratory. Example materials that can be included in the housing 502 include plastics, metals, and composites. The housing 502 can be constructed of multiple or a singular material and can include geometry and/or structural features that enhance the usability of the reader 500. Such features can include a smooth outer surface that is easily cleaned, grips or handles for carrying the reader 500, shock protection and/or increased structural strength in locations to prevent damage to the internal components of the reader 500, insulation and/or heat dissipation structure(s) assist with maintaining a desired and/or a stable temperature, or range, within the housing 502, a membrane or construction to prevent the intrusion of moisture and/or dust into the interior of the reader 502, connections, ports and/or interfaces for connecting the reader 500 to an external element and/or device using a physical or wireless connection, instructions regarding the use of the reader 500, identification markings such as a serial number and/or additional necessary or desirable features that can facilitate the safe, effective, efficient and/or proper use of the reader 500. The housing 502 can feature access points, such as removable or openable panels, to allow access to the interior of the reader 500 for maintenance and/or repair of the internal components, elements and/or systems of the reader 500. Additionally, the housing 502 of the reader 500 can be removable or separable from the other components, elements and/or systems of the reader 500, allowing the replacement of the housing 502, easing the cleaning of the housing 502, providing access to the components, elements and/or systems of the reader 500 and/or other abilities that require and/or made easier by the removal of the housing 502 of the reader 500.

The portability of the reader 500 can be an important consideration in the design and packaging of the reader 500, including the housing 502. The reader 500 may need to be rugged and easily transported so that it can be moved to and used in a variety of embodiments. Considerations, such as operating environment and access to infrastructure, can be considered when designing and/or constructing the reader 500 such that the reader can be used safely, effectively, and efficiently in a variety of environments and/or locations reliably. Depending on the environment of and infrastructure available in a particular location in which the system is to be used, the housing can be customized to best operate in that location by the addition and/or modification of existing reader features. Alternatively, the reader 500 can be designed and/or packaged to be more permanently located, such as in a laboratory, clinic, or other setting.

The housing 502 of the reader 500 includes a cartridge interface 504 that interacts with and/or engages the cartridge 560 for analysis of a patient sample. The cartridge interface 504 can be a slot that is shaped to receive the cartridge 560. Alternative designs and/or structures of cartridge interfaces 504 can be used with the reader 500. Additionally, the cartridge interface 504 can include additional structures, such as a door, that can effect insertion of the cartridge 560 within the reader 500. The user inserts the cartridge 560 into the slot in preparation for analysis of the patient sample. The slot can include internal geometry that aligns and/or orients the inserted cartridge 560 in a proper alignment and/or orientation for the components, elements and/or systems of the reader 500 to perform the requisite or desired analysis of the patient sample contained within the cartridge 500. For example, the cartridge interface 504 can accept a variety of cartridges 560 having different cross-sections, such as square, rectangular, and circular cross-sections. The unique shape of each cartridge 560, the unique cross-section, can interact with the geometry of the cartridge interface 504 to properly align the cartridge 560 within the reader 500 for analysis. For example, the circular cross-section cartridge can insert into the cartridge interface 504 to a first position at a first orientation, the square cross-section cartridge can insert into the cartridge interface 504 to a second position at a second orientation. The various orientations and positions a specific cartridge 560 can be inserted into the cartridge interface 504 can be the same or different for multiple condition/disease-specific cartridges 560.

The reader 500 can also include a cartridge verification system 540. The cartridge verification system 540 can be integrated with or separate from the cartridge interface 504 and/or included internal to or external from the reader 500. The cartridge verification system 540 can verify the legitimacy of a cartridge to assist with efficient and effective analysis of a patient sample. An example verification system 540 can include a verification element 569 of the cartridge 560 that interacts with the cartridge verification system 540 to verify the cartridge prior to further processing of the patient sample. Additionally, verification of the cartridge 560 can include determining that the cartridge has not been previously used. The reuse of cartridges can be allowed or not and the verification system 540 can be used to enforce the desired or required limitation on reuse of the cartridge 560. Once the cartridge is verified, further analysis of a patient sample contained within the cartridge can be allowed to proceed. The verification of the cartridge can be the threshold analysis of the in vitro diagnostics process of the patient sample, in some examples. This verification can include limiting the analysis to a specific single or multiple analyses based on the cartridge verification.

A positive engagement or lock in the reader 500 can engage the cartridge 560 when properly and fully inserted. This engagement can also provide a tactile, audible, and/or visual cue to the user to signify proper insertion or interfacing of the cartridge 560 and reader 500. An example positive engagement or lock can include a notch and protrusion arrangement, the notch is sized to receive and releasably restrain the protrusion when engaged such that the notch of one element, the reader 500 or cartridge 560, engages the protrusion on the opposite element, reader 500 or cartridge 560, to releasably connect, interface with and/or engage the two elements, the reader 500 and cartridge 560, together. When prompted, such as when the analysis is completed or an error situation, the user can remove the cartridge 560 from the reader 500.

The cartridge interface 504 can also include an actuator or other element of the reader 500 that assists with the proper insertion and/or interfacing of the cartridge 560 and reader 500. The actuator can engage the cartridge 560 before the cartridge is fully inserted, the actuator can then position the cartridge 560 in a proper alignment and/or orientation with the reader 500 for the reader 500 to analyze the patient sample within the cartridge 560. When prompted, such as automatically by the reader 500 or manually by the user, the actuator can "eject" or disengage the cartridge 560 from the reader 500. The disengagement can fully or partially remove the cartridge 560 from the reader 500. Alternatively, the actuator can assist with the engagement or interfacing of the cartridge 560 with the reader 500 and not with the disengagement of the cartridge 560 and reader 500. In this example, the user can be required to remove the cartridge 560 from the reader 500 when prompted.

The cartridge interface 504 can be shaped to engage one or more specific cartridges 560, which prevents the insertion of an incorrect or improper cartridge 560 within the reader 500. The cartridge interface 504 can also be reconfigurable, either manually by a user or automatically by the reader 500 to accommodate a specific cartridge design to perform one or more specific analyses of a patient sample. For example, a user can input a desired or required analysis to be performed on a patient sample, the reader 500 can then reconfigure or prompt the reconfiguration of the cartridge interface 504 to accept a specific cartridge 560 that corresponds to the requested analysis.

For example, the cartridge interface 504 can include multiple configurable elements, such as panels, that can be configured and/or arranged automatically in response to a received analysis to be performed, such as a user-selected disorder, condition, infection or disease for which to analyze the patient sample. The now configured and/or arranged configurable elements of the cartridge interface 504 are in a specific geometry into which only a compatible cartridge can be inserted. The analysis to be performed can be an input by a user into the reader 500 or from a remote administrator or system. In a further example, a specific cartridge interface 504 can include removable and/or replaceable cartridge interfaces 504 that can be removed from and/or inserted in the reader 500. Each cartridge interface can include geometry to accept a specific cartridge design(s). Additionally, the inserted cartridge interface 504 can be detected or otherwise communicated to the reader 500 and the reader 500 can limit available options, such as the analyses that can be performed, based on the inserted cartridge interface 504. Each cartridge interface 504, or cartridge interface 504 design or geometry, can correspond to a specific analysis or analyses. Further, the reader 500 can be limited to the specific analysis or analyses corresponding to the particular cartridge interface 504 and/or cartridge interface 504 geometry.

In a further example, the cartridge interface 504 can initially accept any inserted cartridge. Once a cartridge is inserted, the cartridge interface 504, a sensor or other reader 500 system or element can detect the cartridge type and the corresponding analysis or analyses that can be performed based on the cartridge type. The cartridge interface 504 can manipulate the cartridge position and/or orientation, the reader 500 can properly position and/or orient analysis systems or elements relative to the cartridge, and/or the cartridge interface 504 and/or reader 500 systems or elements can be configured to perform the analysis or analyses corresponding to the cartridge type.

Also, a sample processing module 532 of the processing circuitry 530 of the reader 500, or an external sample processing system and/or element, can alter the processing of the sample analysis data to correct, compensate or otherwise modify the collected sample analysis data based on the type of cartridge inserted within the reader 500. Instead of or in addition to positioning and/or aligning the cartridge and/or reader 500 analysis systems relative to the reader, the processing of the collected sample analysis data can be manipulated and/or modified to compensate based on the type of cartridge inserted. Additional modifiers can include compensating for position/alignment errors caused by improper alignment/positioning of the cartridge relative to the analysis systems and/or elements.

Further, the cartridge interface 504 can include multiple orientation and/or alignment features that engage specific cartridge 560 features to properly align a specific, inserted cartridge with a specific analysis process. For example, a first cartridge for a first specific analysis is inserted into the cartridge interface 504 which guides, aligns, and/or orients the first cartridge properly in a first position for the first analysis to be performed, a second cartridge for a second specific analysis can be interested in the same cartridge interface 504, which can properly guide, align, and/or orient the second cartridge in a second position for the second analysis to be performed. In this manner, the cartridge interface 504 ensures the proper positioning of a variety of specific cartridge designs within the reader 500 allowing a corresponding variety of specific analyses to be performed, each analysis corresponding to one or more specific cartridge designs.

The cartridge interface 504 can also include a number for position points corresponding to various steps of analysis. For example, an analysis can require that the cartridge 560 is inserted partially to a first position within the reader 500 to perform a first step of the analysis, the reader 500 can prompt the user to advance or move the cartridge 560 to a second position, such as further insertion of the cartridge 560 within the reader 500, to perform a further step of the analysis. Each position can include a tactile, audible, or visual indication to a user manually inserting the cartridge 560 within the cartridge interface 504 to assist the user with properly position the cartridge 560 within the cartridge interface 504. An actuator, such as described previously, can position the cartridge 560 at the various analyses required positions automatically, or can assist the user with the cartridge 560 positioning.

Insertion of the cartridge 560 into cartridge interface 504 of the reader 500 can automatically initiate or prompt a user to initiate analysis of the patient sample contained within the cartridge 560. An actuator and/or sensor can be connected to the processing circuitry of the reader 500 and triggered by and/or sense the insertion of the cartridge 560 to automatically initiate or to prompt a user to initiate the analysis of the patient sample. Initiating analysis of the patient sample can include powering-up, preparing, and/or running the various analyses systems and/or devices, such as an electrophoresis module 506 and an electrophoresis band detection module 508. In some examples, the user need only insert the cartridge 560 in the reader 500 to actuate or trigger the entire diagnostics process to an output.

The cartridge interface 504 and additional elements, such as guides or actuators can be integrated into the housing 502 of the reader 500 or can be separate components, elements and/or systems. Each of the additional elements can be further separable from each other allowing for replacement, substitution, repair and/or maintenance of the additional elements as necessary or required.

The reader 500 can include a single cartridge interface 504, such as the example shown in FIG. 1, or can include multiple cartridge interfaces 504 in the same reader 500. The multiple cartridge interfaces 504 can allow the reader 500 to analyze multiple patient samples simultaneously and/or in succession by allowing more than one cartridge 560 to be interfaced with the reader 500. Additionally, each of the multiple cartridge interfaces 504 can accept the same and/or different cartridges to perform the same and/or different analyses. Further, in conjunction with a multi- or singular cartridge interface 504, a guide, rack, carousel and/or system can hold multiple cartridges in preparation for analysis. The guide, rack, carousel and/or system can feed or guide, actively or passively, cartridges 560 to the reader 500 by the cartridge interface 504 allowing multiple patient samples and/or cartridges 560 to be analyzed with minimal interruption between the analyses.

The reader 500 shown in FIG. 5 includes an electrophoresis module 506 that can interface with the cartridge 560 to perform the electrophoresis test. The electrophoresis module 506, alone or in conjunction with the processing circuitry 530, can control the electrophoresis test, including voltage/current application time and/or level. The electrophoresis module 506 can supply electrical power from a power source 510 of the reader 500 to the cartridge 560, or electrophoresis strip 564 directly, to establish the necessary voltage across the electrophoresis strip 564 for testing. The voltage can be applied at a higher level to increase the speed of the testing, however, the increased speed can cause decreased band fidelity, which can increase the difficulty and error of the band analysis and evaluation. A lower applied voltage can increase band fidelity but can lengthen the required testing time. Alternatively, the electrophoresis module 506 can vary the applied voltage or current, while maintaining the other stable, to achieve a desired or required level of band fidelity and testing speed. For example, an initial test to identify a patient condition can be carried out at a higher level voltage level to speed the test and a subsequent test to quantify the condition can be carried out a lower voltage level to generate clearer or more accurate results.

The electrophoresis band detection module 508, alone or in conjunction with 530, can capture, analyze and/or evaluate the electrophoresis test results and/or any other band detection characteristic(s) related to or otherwise based on the electrophoresis test results. The electrophoresis band detection module 508 can include an imaging device, such as a digital image sensor, to capture an image of the electrophoresis strip and the banding thereon at the conclusion of the electrophoresis test. Using the captured image data, each of the bands can be associated with one or more compounds/components of the patient blood sample and the proportions of each can be determined.

The reader 500 can also include an optional sample treatment 550. The sample treatment 550 can include a buffer solution for use with the electrophoresis strip, markers to add to the blood sample, dilutants and/or other solutions/compounds for use in the electrophoresis testing. The sample treatment(s) 550 can be contained within removable cartridges to ease replacement and/or change of the sample treatment 550. Alternatively, the reader 500 can include internal containers for storing the sample treatment 550. Associated tubing, systems and/or components can be included to facilitate the transfer of the sample treatment 550 to the cartridge and/or other systems/components of the reader 500.

The positioning and structure of the cartridge 560 within the reader 500 can be such that one or both of the electrophoresis module 506 and the electrophoresis band detection module 508 are properly aligned with the cartridge 560 when inserted into the reader. The electrophoresis module 506 can interface with contacts on the cartridge 560, or the electrophoresis strip 564 itself, to supply the necessary voltage to the electrophoresis strip 564. The electrophoresis band detection module 508 can be aligned to monitor and/or capture an image of the electrophoresis strip 564 during and/or after the electrophoresis test.

The reader 500, the electrophoresis module 506 and/or the electrophoresis band detection module 508 can include an optional light source 555. The light source 555 can illuminate the electrophoresis strip 564 to assist with capturing the electrophoresis results for analysis. Light emitted by the light source 555 can be reflected from and/or transmitted through the electrophoresis strip 564 to assist with imaging the electrophoresis strip 564. Additionally, the light emitted by the light source 555 can have constant and/or varying properties, such as a wavelength, intensity and/or a frequency of the emitted light. The light source 555 can include one or more illumination elements to generate light having the required, or desired, properties to assist with imaging and/or analyzing the electrophoresis results.

The reader 500 can include an internal power source 510 that supplies the necessary power to run the components, elements and/or systems of the reader 500 to perform analysis of patient samples and/or preserve a minimal, required functionality of the reader. The power source 510 can supply power to the processing circuitry 530, the electrophoresis module 506, the electrophoresis band detection module 508 and/or other component, elements and/or systems of the reader 500. The power source 510 can include one or more batteries or other energy storage devices that provide a required or desired level of power for the reader 500. Additionally, the power source 510 or a portion thereof can be external to the reader 500 and connected thereto as needed or required. External power sources can include batteries or other energy storage devices and/or a connection to a nearby power source such as a generator, municipal power, or solar array.

The reader 500 can also include pathogen neutralization 512. The pathogen neutralization 512 can include physical components, such as a device or system, and/or a chemical component. There are many different methods of pathogen neutralization and many different devices/systems capable of performing the methods. The goal of pathogen neutralization is to target specific undesirable biological material, such as diseases and parasites, for destruction/neutralization or to destroy biological material indiscriminately, such as by sterilization. Various systems, such as devices or chemicals that interrupt biological processes and/or cause the breakdown of biological materials can be to neutralize pathogens within a reader 500 and/or a cartridge 560.

An ultraviolet (UV) light source is an example pathogen neutralization 512 device that could be used within the reader 500 is e. Exposure to UV light has a debilitating effect on biological material and exposure to intense UV light can cause biological destruction. A UV light source can be placed within the reader 500 and activated to bathe the interior of the reader in UV light, which neutralizes at least a portion of the biological material, including pathogens, within the reader 500. Alternatively, the UV light can be continuously powered on when the reader 500 is in use. The UV light can also be targeted, with one or more UV light sources placed in specific areas of the reader 500 to perform the desired pathogen neutralization. Additionally, the UV light can be positioned to penetrate and/or bathe a cartridge 560 inserted within the reader 500 to neutralize the patient sample within the cartridge 560 after analysis has been performed. A timing device can be connected to the UV light source to ensure that the UV light source is activated for a necessary amount of time to perform the pathogen neutralization. A photo- or light detector can also be included to monitor the output of the UV light source to check the continued efficacy of the UV light source and/or monitor the output of the UV light source to ensure it is activated for a long enough duration to achieve a level of pathogen neutralization. The emitted UV light can affect materials, such as plastic, adversely causing them to become brittle. In some examples, shielding can be included within the housing 502 of the reader 500 to protect areas, components, elements and/or systems which could be damaged by UV light exposure.

A further pathogen neutralization 512 system can include the use of chemicals to neutralize biological material within the reader 500 and/or cartridge 560. A chemical based pathogen neutralization 512 system can include the application of chemicals within the reader 500 and/or cartridge 560 on a temporary or permanent basis. That is, a chemical application can be applied within the reader 500 during manufacture, the applied chemical application can continuously destroy at least a portion of biological material that contacts a surface upon which the chemical was applied. A temporary chemical based pathogen neutralization 512 system can include a chemical dispersal system that deploys or applies chemicals within the reader 500 and/or cartridge 560 on actuation, the chemicals contact various surfaces, elements, components and/or systems of the reader 500, destroying at least a portion of biological material thereon.

In an example embodiment, pathogen neutralizing chemicals, such as a bleach-based solution, can be sprayed, fogged, and/or distributed about the interior of the reader 500 and/or cartridge 560 to perform the pathogen neutralization. The pathogen neutralizing chemicals can be added to the reader 500 and/or cartridge 560 by a user, contained within a vessel that is housed, inserted within or fluidically connected to the reader 500. The pathogen neutralizing chemicals, such as the bleach-based solution, can be prepared as needed or can be prepared and stored for later use. An indicator or timer can be included that can indicate to a user once the pathogen neutralization process is complete. The indicator or timer can also prevent the use of the reader 500 until the pathogen neutralization process is complete. As with the previously described pathogen neutralization systems, the chemical-based pathogen neutralization method can also neutralize at least a portion of biological material on and/or within a cartridge 560 inserted within the reader 500. Additionally, the chemical-based pathogen neutralization chemicals can be pumped or transported through the various components, elements and/or systems of the reader 500, to disinfect portions that can contact a patient sample, which helps to prevent cross-contamination of patient samples.

An example pathogen neutralization system to neutralize at least a portion of the pathogens of the cartridge 560 can include a portion that is included in the cartridge 560. Pathogen neutralization material, such as powders, fluids and/or other components can be included in the reader 500 and/or cartridge 560 assist with neutralization of pathogens within the cartridge 560. The pathogen neutralization material can be included in a portion of the cartridge 560 and dispersed into the collected sample and/or other portions of the cartridge 560 upon actuation, such as by a user, the reader 500, the cartridge 560, or another source. The pathogen neutralization material can also be integrated with a portion of the cartridge. Alternatively, the pathogen neutralization material can be included in the reader 500 and the reader 500 can circulate, or otherwise insert, the pathogen neutralization material into the cartridge 560. The pathogen neutralization material can be targeted to a specific pathogen or be a general wide spectrum pathogen neutralizer.

The reader 500 can include an output 514 that includes one or more visual 516 and/or audible 518 outputs although in other examples the output is data and does not include visual and/or audible outputs. The output 514 shown in FIG. 5 communicates information regarding the status of the reader 500, the results of analysis of a patient sample, instructions regarding use of the reader 500 and/or other information to a user or other computing device. The visual 516 output 514 can include a display, such as a screen, such as a touchscreen, lights, and/or other visual indicators. The touchscreen used to display information, such as analysis results, to the user can also be used by a user to input to the reader 500. Alternative interfaces can be included on and/or connected to the reader 500, such as a keyboard and/or mouse. Additionally, user devices, such as a cellphone or tablet, can be connected to the reader 500 to provide an interface portal through which a user can interact with the reader 500. The audible 518 output 514 can include a speaker, buzzer, or other audible indicators. The output 514, visual 516 and/or audible 518, can be output through an external device, such as a computer, speaker, or mobile device connected physically and/or wirelessly to the reader 500. The output 514 can output data, including the collected analysis data and/or interpretative data indicative of the presence or absence of a disorder, condition, infection and/or disease within the patient and/or the patient sample. An example can include the identification and proportions of the various hemoglobin types within the patient sample. The interpretive data output can be based on the analysis data collected and processed by the processing circuitry 530 of the reader 500.

The reader 500 can also include temperature control 520. The temperature control 520 can actively and/or passively control the temperature of at least a portion of the reader 500. Active temperature control 520 can include heating and/or cooling a portion of the reader 500 and/or cartridge 560. Temperature control 520 can also include heating one portion of the reader 500 and/or cartridge 560 and cooling another portion of the reader 500 and/or cartridge 560. The temperature control 520 can include a refrigeration system, resistive heater, infrared heater, thermoelectric elements, radiator, and/or other temperature control devices and/or systems. Passive temperature control can include structures to contain a thermal material in portions of the reader 500 and/or cartridge 560. This can include holders for ice, hot water, ice packs, and other thermal materials, the holders retain the thermal material in portions of or about components, elements and/or systems of the reader 500 and/or cartridge 560.

The reader 500 and/or cartridge 560 can also include a filter. The filter can attract, extract, collect and/or otherwise remove unwanted components or particles in a patient sample of the cartridge 560 or concentrate the wanted components or particles. The filtering of the patient sample by the filter can occur as the patient sample is transferred from the cartridge 560 into the reader 500 or the patient sample can be transferred from the cartridge 560, through the filter and back into the cartridge 560 for analysis or internal to the cartridge 560. The filter can include structural and chemical features that allow the filter to remove desired or required components from the patient sample. The filter can be affixed in a stationary position to contact the patient sample or moveable through the patient sample to filter the patient sample.

Processing circuitry 530 can be included in the reader 500 to receive input from various components, elements and/or systems, such as the electrophoresis module 506 and/or the electrophoresis band detection module 508, of the reader 500. The processing circuitry 530 can process the received inputs to perform analysis of the patient sample and output results and/or data of that analysis. The processing circuitry 530 can include a sample processing module 532, a network module 534, a maintenance module 536 and a database 538. The various elements, 532, 534, 536, 538 and others, of the processing circuitry 530 can be removable and/or replaceable, allowing replacement and addition of various elements to the processing circuitry 530. In example embodiments, all or a portion of the processing circuitry 530 can be included in the reader 500 and a portion of processing circuitry included in the cartridge 560. The processing circuitry 530 can also control the various components, elements and/or systems, such as pathogen neutralization 512, the electrophoresis module 506, the electrophoresis band detection module 508, and others, of the reader 500.

The processing circuitry 530 can initiate and/or control the analysis of a patient sample within a cartridge 560. The processing circuitry 530 can include preset routines, which may be defaults or selectable by the user, that can be executed by the reader 500 to analyze a patient sample. The preset routines can include prompts for user input and/or the processing circuitry 530 can prompt a user for input before, during and/or after analysis of a patient sample. User prompts can include acknowledgement and/or authorization to proceed through one or more portions of the analysis process. Alternatively, the processing circuitry 530 can initiate, perform, and/or direct the analysis of the patient sample automatically without user prompts. The processing circuitry 530 can proceed through the various processes and procedures of an analysis of a patient sample, engaging any one or more of the reader 500 systems and collecting the analysis data. The processing circuitry 530 can further automatically process the collected data and transmit a result to a user or other, including an indication the analysis is complete, information regarding the analysis and/or other indications. The processing circuitry 530 can also transmit the collected data to an external system or device for processing and can transmit a result to the user and/or the result can be transmitted by one or more of an external system and/or device.

The sample processing module 532 can receive inputs from the electrophoresis band detection module 508. Based on the received band detection data the sample processing module 532 can determine at least a characteristic of the patient sample, such as a disease or condition, an identity of the various compounds/components of the patient sample and quantification of the various compounds/components of the patient sample. The sample processing module 532 can output the identification and proportions of the compounds/components, and/or other various data based on the analysis of the patient sample. For example, the sample processing module 532, using the band detection data from the electrophoresis band detection module 508, can identify and quantify the various hemoglobin types of the patient sample. The output from the sample processing module 532 can be transmitted through the output 514 of the reader 500 or transmitted to an external device and/or system, such as a computer, mobile device, and remote server or database.

The sample processing module 532 can analyze the patient sample to determine a hemoglobin characteristic, such as a hemoglobin affecting disease and/or condition, based on the data from various components, elements and/or systems of the reader 500. The results of the analysis can be output from the sample processing module 532 to the output 514 to convey the information to a user or other.

A network module 534 can be included in the processing circuitry 530. The network module can allow the reader 500 to communicate with other readers, computing devices, servers, databases and/or other devices or systems. The network module 534 can communicate with another device through a physical, such as a local area network (LAN), Universal Serial Bus (USB), and/or wireless, such as Bluetooth®, connection. In an example, the reader 500 can communicate to a remote server through the network module 530 allowing the reader to upload patient sample analysis to the patient's medical records stored on the remote server. The network module 534 can transmit and/or receive communication to/from the reader 500 and another device or system. In another example, information on the patient can be downloaded to the reader and added to the display or output or used in the analysis(es). For example, demographic information such as age, sex, etc. Information on prior results or health history could also be used to modify the analysis performed in the Reader 500.

A maintenance module 536 can be included in the processing circuitry 530. The maintenance module 536 can perform, initiate and/or prompt maintenance, calibration, and/or other processes of the reader 500. Maintenance of the reader 500 can include automatically, or by prompting a user, clean a portion of the reader 500, replenish resources of the reader 500 and other regular or unscheduled maintenance of the reader 500. Calibration of the reader 500 can include testing components, elements and/or systems of the reader 500 to check if the reader 500 is in an effective operable state and/or to adjust measurement or analysis parameters to take the measured state of the machine into account. Additionally, the calibration of the reader 500 can be performed by the maintenance module 536 and/or prompt a user to perform necessary calibration procedures to allow the reader 500 to perform patient sample analysis effectively and correctly. The maintenance module could also allow automated or semi-automated ordering of supplies or service.

A database 538 can be included in the processing circuitry 530. The database can record images, patient sample analysis data, patient data, statistical data, test conditions, and other data. The network module 534 can communicate with the database 538 exporting and/or importing data. The database 538 can be stored on removable and/or permanent data storage within the reader 500. The database can also occur in whole or in part remote from the reader.

Statistical data of the database 538 can be used during analysis of a patient sample by the sample processing module 532 to assist and/or perform the analysis of a patient sample. Additionally, the database 538 can include statistical analysis techniques and/or algorithms that can be used by the sample processing module 532 to determine, calculate or otherwise analyze the patient sample. The database 538 can also include specific information, such as prior patient analysis results. Such results can be used to determine if the detected condition is new and/or an existing condition. Additionally, the severity of the condition can be tracked for a particular patient to assess their treatment progress.

The cartridge 560 can contain the patient sample for analysis. The cartridge 560 can be inserted in the cartridge interface 504 and the patient sample analyzed or transferred to the reader 500 for analysis by the components, elements and/or systems of the reader 500. The cartridge 560 can include a blood collection device or system 562, an electrophoresis strip 564, a buffer 566, a temperature control device and/or system 568 and a verification element 569.

Blood collection 562 of the cartridge 560 can include a device and/or system for collecting, storing, and/or analyzing a patient's blood sample, which can include a passive or active blood collection device or system, a blood sample storage chamber, a blood sample analysis chamber and/or other chambers, devices and/or systems to assist or facilitate the collection of a blood sample and analysis of the blood sample.

Active blood sample collection can include the use of a needle, capillary tube or pipette. In an example embodiment, the cartridge 560 can include a needle that can be actuated to deploy from the cartridge 560, piercing a patient's skin and extracting a sample that is drawn into the cartridge 560 and stored for analysis. A further active blood sample collection 562 can be a pipette-like system. The user or other can apply pressure to a bulb or deformable portion of the cartridge 560, the release of pressure on the bulb or deformable portion can draw at least a portion of a patient blood sample into the cartridge 560. The patient can be lanced, poked or pierced to cause bleeding, the blood can be sampled to draw at least a portion of the blood into the cartridge 560 for analysis.

The blood collection 562 can include a lancet or a piercing instrument that can pierce skin to cause bleeding. The blood can be collected using the cartridge 560 to obtain the patient blood sample. Collection of the blood sample can include retraction of the lancet or piercing instrument, carrying a portion of the patient blood into the cartridge 560 for analysis. The blood collection 562 can also include a sealed chamber that has a negative internal pressure. A needle can pierce the patient and pierce the sealed chamber, the negative pressure of the sealed chamber causing blood to flow into the sealed chamber due to the pressure differential.

The blood collection 562 can also include a capillary tube that can passively collect a blood sample using capillary action. The patient is caused to bleed, such as by a lancet or other inducing technique, and the capillary tube is placed in the blood to draw a sample into the capillary tube of the cartridge 560 for analysis.

The cartridge 560 can include a filter to filter the patient sample within the cartridge 560. The filter can be placed to filter the patient sample as it is drawn into the cartridge 560 through, before and/or after the blood collection 562. In another example, the filter can filter the sample after it has been stored in the cartridge 560. As previously described, the filter can include structural and/or chemical features to filter a patient sample as necessary or desired.

Preparation of the patient sample can include lysing of the patient sample. The reader 500 can also include mechanical lysing. Mechanical lysing can assist with the lysing of cells of a patient blood sample within a cartridge 560 or the lysing of the patient blood sample within the reader 500. Mechanical lysing can include a physical disruptor, or portion thereof, an agitator, a sonicator that can apply sound energy to the patient sample, filtering of the patient sample and/or other mechanical lysing device or system. The mechanical lysing can interface with and/or engage the cartridge 560 to facilitate the lysing of the patient sample. The mechanical lysing can be mechanically powered, such as by a wound spring, or electrically powered, such as by a reader 500 power source 510.

Alternative methods of lysing can include chemical lysing of the patient sample. Chemical lysing can include mixing the patient sample with one or more compounds and/or substances to cause lysing of the patient sample. For example, the patient sample can be mixed with a dilutant, such as water, that is selected to cause lysing of the patient sample. As with mechanical lysing, a requisite amount of time can elapse before analysis of the patient sample is performed in order to allow adequate lysing of the patient sample to occur.

The electrophoresis strip 564 of the cartridge 560 is a piece of material on or through which the electrophoresis test occurs. The electrophoresis strip 564 can be a variety of shapes, such as a strip, and composed of a variety of different materials, such as cellulose acetate, glass fibers or agarose gels. The cartridge 560 can include an opening in which the electrophoresis strip 564 is positioned and/or accessible to one or more systems/components of the reader 500, such as the electrophoresis module 506 and/or electrophoresis band detection module 508. Alternatively, the cartridge 560 can include a transparent or translucent portion(s) about electrophoresis strip 564 through which suitable imaging of the electrophoresis strip 564 can be performed to obtain the electrophoresis results.

A buffer 566, for use with the electrophoresis strip 564, can be included in the cartridge 560. The buffer 566 can be a conductive solution that may also modify the chemical environment the test is run in, for example by controlling the pH, that is applied to the electrophoresis strip 564 prior to an electrophoresis test. Certain materials of the electrophoresis strip 564 can require the use of a buffer 566 to perform an electrophoresis test. A chamber of the cartridge 560 can store the buffer 566 and the reader 500 or user can cause the buffer 566 to be applied to the electrophoresis strip 564. Alternatively, a buffer can be stored within the reader 500 and applied to the electrophoresis strip 564 prior to a test. The cartridge 560 can include various routing to transfer the buffer 566 from an internal chamber of the cartridge 560 or from the reader 500 to the electrophoresis strip 564.

Additional sample treatment solutions and/or materials, such as a dilutant, can be included in the cartridge 560. Dilutant can be used to dilute, treat and/or prepare the patient sample for analysis. The dilutant can be stored within the cartridge 560 separate from the patient sample and mixed automatically or manually. The dilutant can be preloaded in the same chamber, a mixing chamber or patient sample chamber in which the patient sample is stored within the cartridge 560. The user could also add the dilutant or it could be stored in the reader.

The cartridge 560 can also include temperature control 558, which can include active and/or passive temperature control systems and/or methods. Passive temperature control 558 can include insulation, structural design features and/or chemical design features. The passive temperature control 558 can maintain the temperature of the cartridge 560 to preserve a collected patient sample. Active temperature control 558 can include electronic elements, such as thermoelectric elements that can heat or cool at least a portion of the cartridge 560, for example to regulate the temperature of the cartridge 560 or a portion thereof. Temperature control 558 can include heating and/or cooling the temperature of the cartridge before, during and/or after the collection of a patient sample and/or the analysis of the sample. The temperature control 558 interfaces with the reader 500 and/or an external device to regulate the temperature of the cartridge 560.

Figure 6:
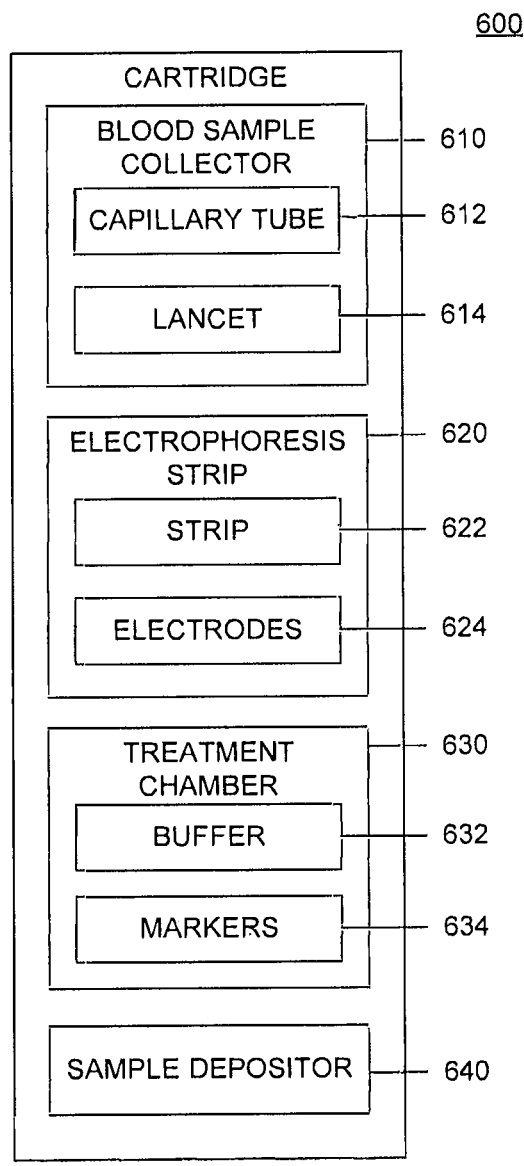
FIG. 6 is a block diagram of another example cartridge.

FIG. 6 is a further example cartridge 600, which can include a blood sample collector 610, an electrophoresis strip 620, a treatment chamber 630, and/or a sample depositor 640. The various components of the cartridge 600 can be arranged in various configurations depending on the analysis to be performed and/or other environmental and/or use considerations. In the example shown in FIG. 6, the cartridges 600 components can be interchangeable allowing a complete cartridge 600 to be assembled from various components.

The blood sample collector 610 of the cartridge 600 can collect a blood sample from a patient. The collector 610 can include devices, components and/or systems to assist or perform the collection of the blood sample from a patient. The blood sample collector 610 can include a capillary tube 612 and/or a lancet 614. The capillary tube 612 can use capillary action to draw a blood sample into the cartridge 600. The lancet 614 can be used to pierce, puncture and/or cut a patient's tissue to cause bleeding, from which a blood sample can be taken.

The collected blood sample can be collected in a blood sample chamber of the cartridge 600. The blood sample chamber can include a filter to filter the blood sample. The filter can be positioned within the blood sample chamber of the cartridge 600 such that the blood sample chamber is divided into a first and second portion, which are separated by the filter. The blood sample chamber can include structural and/or chemical features to assist with the storage of the blood sample and/or the analysis of the blood sample. Additionally, the blood sample chamber can be located within the cartridge 600 to assist with and/or facilitate the analysis of the blood sample using a reader.

An electrophoresis strip 620 can be included with the cartridge 600. The electrophoresis strip 620 can include a strip of material 622 on or through which the test is conducted and a pair of electrodes 624 to apply the necessary voltage across the strip 622. As previously discussed, the strip 622 can be made of a variety different suitable materials that can support an electrophoresis process. The electrodes 624 can be disposed at opposite ends of the strip 622 to apply a voltage across the strip 622 as part of the electrophoresis testing process. The cartridge 600 can include external contacts that are connected to the electrodes 624 and can interface with a reader device to supply electric power to the electrodes 624. Alternatively, the electrodes 624 and/or the cartridge 600 can include an inductive power mechanism to facilitate the wireless transmission of power to the cartridge 600 and/or the electrodes 624.

The treatment chamber 630 can store one or more materials for use in the electrophoresis process, including a buffer 632 and markers 634. The buffer 632 can be a solution that is applied to the strip 622 prior to an electrophoresis test. The cartridge 600 can include internal structures to facilitate the transfer of the buffer 632 from the treatment chamber 630 to the strip 622. An example buffer can include Tris/Borate/EDTA (TBE) buffer. The buffer solution is electrically conductive and assists with application of a voltage across the strip 622 by the electrodes 624.

Markers 634 can be various compounds/components that can be mixed with the blood sample prior to the test. The markers 634 can have an optical property, such as a color, and known electrophoresis properties, such as moving a known distance along an electrophoresis strip in a set amount of time at a known voltage level. Markers 634 can be selected to move at the same rate as a compound/component of the blood sample or at a different rate. A marker 634 moving at the same rate as a compound/component of the blood sample can be used assist with visualizing a final position of a band associated with that particular compound/component. Alternatively, a marker 634 can be selected so that at the conclusion of an electrophoresis the marker is positioned between two bands of compounds/components of the blood sample or before or after all bands. The marker positioned between or after the two bands can assist with distinguishing the bands from each other during analysis and/or evaluation of the band data.

The treatment chamber 630 can be composed of multiple chambers to isolate the various treatment materials from each other. The cartridge 600 can include various structures to transfer materials from the treatment chamber 630 to various other portions of the cartridge 600. The movement of materials from the treatment chamber 630 can initiated by a reader, user interaction with the cartridge 600 and/or another initiation event or source. A passive process, such as gravity or a capillary action, can be used to move the material from the treatment chamber 630. Alternatively, an active process can be used, such as a pressure differential. A user or reader can power the active transfer process to move the materials from the treatment chamber 630.

The various chambers of the cartridge 600 can be interconnected and/or in fluid communication, allowing and/or facilitating the movement and/or transfer of fluid, with one or more of the chambers of the cartridge 600 and/or a connection to an external fluid source. The fluid communication between chambers can allow the blood sample, the treatment chamber 630 and/or other fluids to flow or be transferred from chamber to chamber(s) and can include passageways like flexible, rigid, and semi-rigid pipes and tubes. Flow control elements, such as valves, can be positioned along one or more of these passageways to regulate the fluid communication between chambers. The flow control elements can be manually actuated, such as by a reader or user applying pressure to the cartridge 600 or actuating the flow control element, or electrically actuated, such as by a signal from the reader or a user initiated signal or trigger.

The cartridge 600 can also include a sample depositor 640, or a portion of a sample depositor system. The sample depositor 640 can deposit an amount of the collected blood sample onto the strip 622 in a controlled manner. A controlled manner can include the amount of blood sample deposited, the area over which the blood sample is deposited, the shape of the area and/or other blood sample deposition characteristics. For the electrophoresis testing, confining the deposited blood sample in a thin, or narrow, line initially can assist with the resultant band fidelity due to the uniform nature from which the compounds/components disperse from the initial deposition of the blood sample onto the strip 622. Example depositors 640 can include a shaped orifice(s) through which an amount of the blood sample can be metered, a shaped applicator that applies a portion of the blood sample to the strip 622 and/or other means. The sample depositor 640 can operate alone, or in conjunction with a reader, to deposit a controlled amount and shape of the patient blood sample onto the strip 622.

Figure 7:
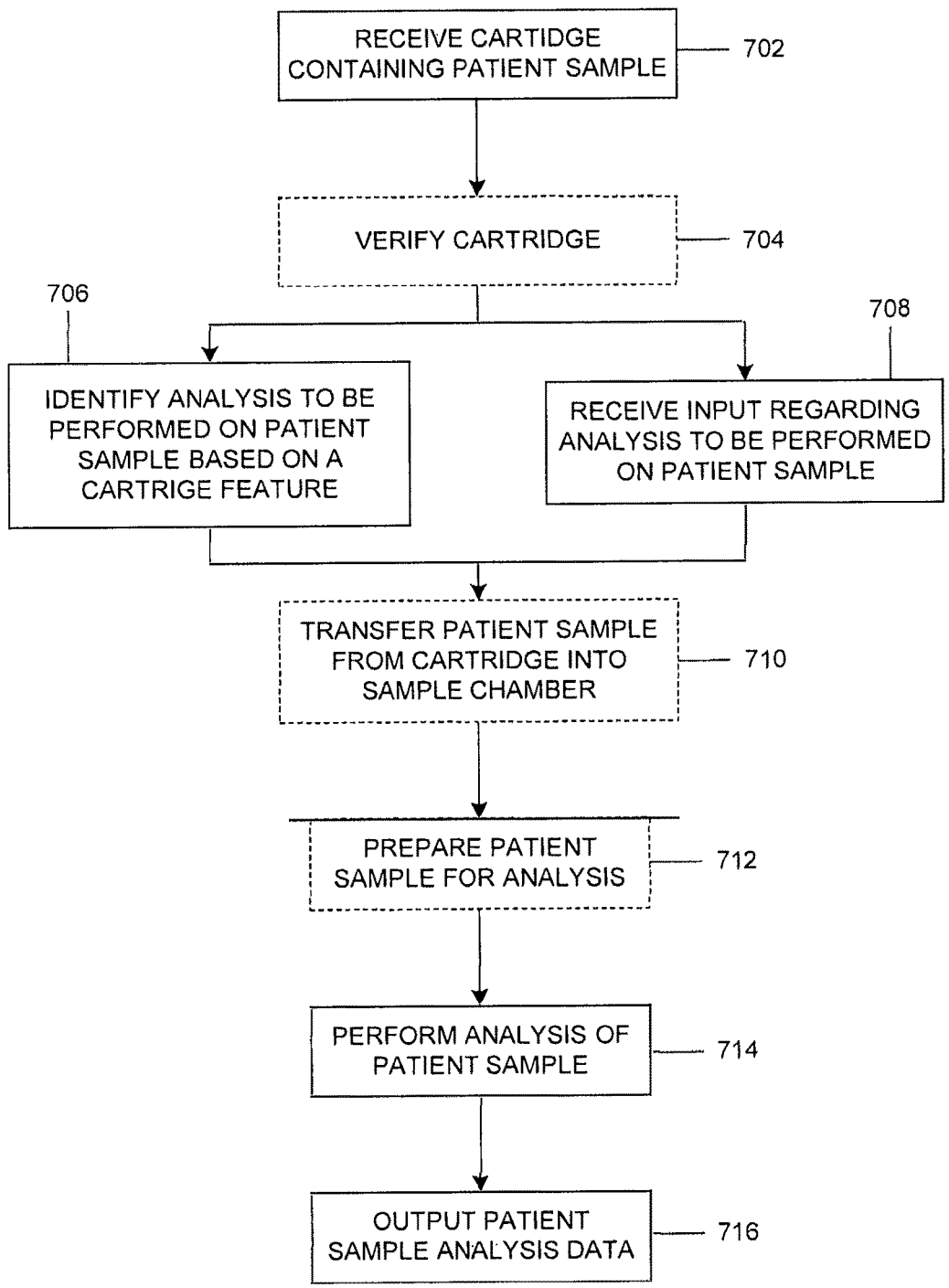
FIG. 7 illustrates an example patient sample analysis process.

FIG. 7 is an example patient sample analysis process 700 of a reader, processing circuitry, a device or system external to a reader and/or a combination thereof. The reader can receive a cartridge containing a patient sample 702, such as the insertion of a cartridge within a cartridge interface, the reader, and/or an external device connected to the reader or an external device or system. The cartridge can be optionally verified 704 to determine the validity of the cartridge and/or the patient sample within. The reader can then identify the analysis to be performed on the patient sample based on a cartridge feature 706, such as structural feature of the cartridge. That is, the reader can recognize or identify the cartridge type and a corresponding analysis that can be performed on the patient sample contained within. Alternatively, the reader can receive an input regarding the analysis to be performed on the patient sample 708. The input can include a user selecting an analysis, communication from an external system or device indicating the analysis performed or other input directing the reader to perform an analysis of the patient sample. Optionally, a portion of the patient sample can be transferred from the cartridge into a sample chamber 710 of the reader so that the patient sample can be analyzed within the sample chamber. Additionally, the patient sample can optionally be prepared for analysis 712, which can include applying a buffer to an electrophoresis strip, adding one or more markers to the patient sample or other preparation performed on or to the patient sample prior to patient sample analysis. The patient sample is then analyzed 714 by the reader and its systems and/or an external device or system. The patient sample analysis data is then output 716, such as transmitted to a reader and/or an external device or system. The output 716 can include measurement, images and interpretive data, such as the presence or absence of a condition, disease and/or infection within the patient sample, including detailed information, such as the type and degree of the disorder, condition, disease and/or infection.

Figure 8:
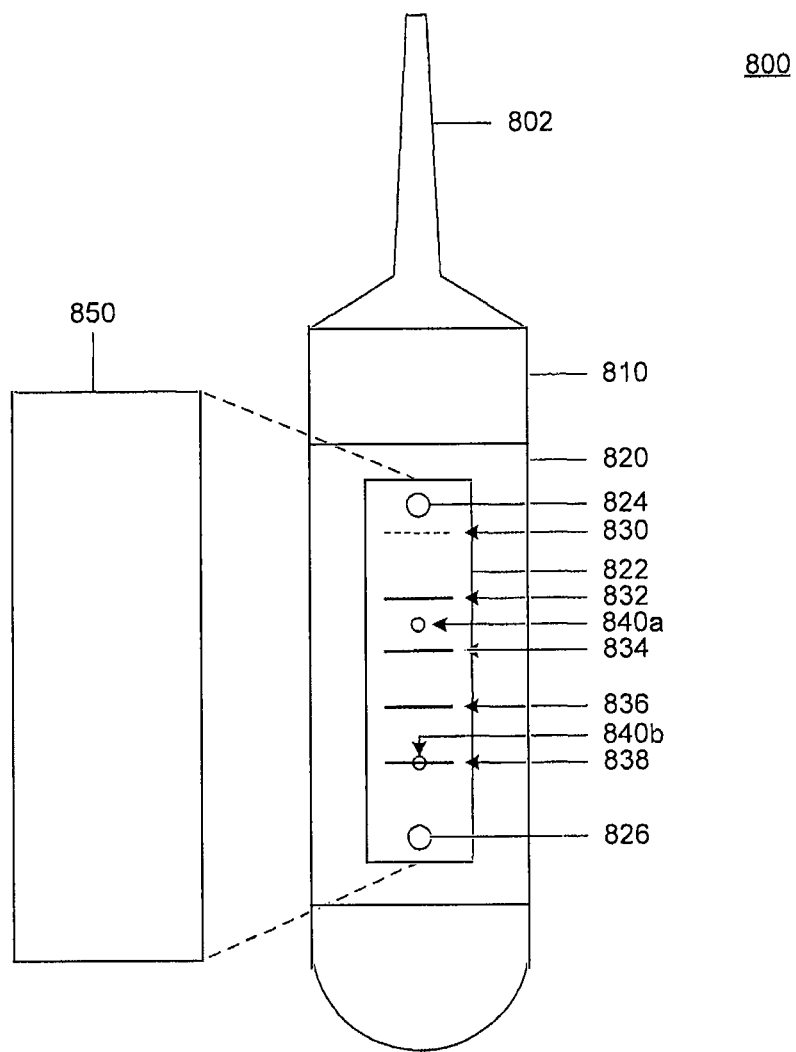
FIG. 8 is yet another example cartridge and electrophoresis detection components.

FIG. 8 illustrates an example cartridge 800 and various patient sample analysis devices/systems in relation to the cartridge 800. The patient sample analysis devices/systems can be included on a reader into which the cartridge 800 is inserted or received, the cartridge 800 can be inserted or received in a specific alignment or orientation in relation to the patient analysis devices/systems of the reader. Additionally, one or more portions of or a complete patient sample analysis device/system can be included with the cartridge 800.

A blood sample collector 802 can be included on the cartridge 800. The blood sample collector 802 can include a capillary or other tube, through which a patient's blood sample can be transferred into the cartridge 800. A capillary tube can use capillary action to draw the blood sample into the cartridge 800. A tube can be part of a pipette or pipette-like device or system of the cartridge 800, application and release of pressure on, or deformation of a portion of the cartridge 800 can cause a blood sample to be drawn through the blood sample collector 802, or portion thereof, due to a pressure differential between the surrounding environment and an internal portion or chamber of the cartridge 800.

The blood sample collector 802 can include a lancet or needle that can be used to cause a patient to bleed and/or with which to take the blood sample from the patient. The lancet or needle can be releasably or permanently affixed to the blood sample collector 802 or can extend and/or retract automatically and/or manually from the blood sample collector 802 to assist or facilitate the collection of a blood sample from a patient.

Alternatively, a patient blood sample can be obtained by other means or methods, and a portion of the patient blood sample can be transferred into the cartridge 800 through the blood sample collector 802 or through another input into the cartridge 800. For example, a blood sample can be drawn from a patient, for use in multiple analysis and/or diagnostic services, using a traditional method such as a needle and vacuum sample tube. From this collected blood sample, a portion of the sample to be analyzed using the cartridge 800 and/or a reader can be transferred into the cartridge 800 for analysis. In this manner, the patient is pierced a minimal number of times, drawing enough blood to run necessary diagnostic tests and analyses, including those using the reader and/or cartridge 800.

The cartridge 800 can be divided into multiple portions and each portion can include one or more internal chambers that can contain a fluid, such as a buffer, dilutant, a marker, a blood sample, or a combination of the blood sample and the marker. One or more internal chambers can also be empty allowing fluids to be introduced and/or mixed within in preparation for analysis and/or additional or alternate purposes. The internal chamber can be interconnected, such as by conduits or tubes, to allow fluid communication between the various chambers. Flow control devices can regulate flow of fluids and/or gases from one or more chamber to another chamber(s). Internal chamber(s) within the cartridge 800 can span across one or more portions of the cartridge 800. That is, a single internal chamber occupies space in both the first portion and second portion of the cartridge 800.

The cartridge 800 can include a sample chamber 810 in which the collected blood sample can be stored and/or prepared for analysis. The sample chamber 810 can be divided into multiple portions, or sub-chambers, to separate the collected blood sample from various treatment materials, such as one or more markers. A first portion can receive the blood sample, which can then be passed through a filter, passively or actively and/or in response to an input, such as by a reader into which the cartridge 800 is inserted, into a second portion of the sample chamber 810 in which the treatment of the blood sample can be performed. The portions of the sample chamber can also be separated by a barrier that prevents and/or controls the flow of the blood sample between the portions of the chamber due to the geometry of the barrier, including openings disposed through the barrier. The barrier can be impermeable and block the flow of the blood sample between the portions of the sample chamber 810 until the barrier is selectively removed, such as by moving the barrier, including by inductively moving or controlling the barrier, or destroying the barrier, including puncturing the barrier, to allow the flow of the blood sample between the portions of the sample chamber 810. Alternatively, the barrier can be dissolvable, completely, or partially, to allow the flow and/or control the flow of the blood sample between the portions of the sample chamber 810. The barrier can also be semi-permeable to control the flow, such as a flow rate, of the blood sample between the portions of the sample chamber 810. In an example, a filter placed between the portions of the sample chamber 810 can be a semi-permeable barrier that controls the flow of the blood sample between the portions of the chamber 810.

A collected sample can be stored within the sample chamber 810 or stored in a different chamber and then transferred into the sample chamber 810 in preparation for analysis. Additional materials or fluids can be added to the sample chamber 810 to mix with a sample in preparation for analysis. Additionally, the sample chamber 810 can be preloaded with various materials or fluids that can be mixed with the sample in preparation for analysis, including stabilizing or preserving the sample, dilution of the sample, markers, reagents and/or other processes or procedures.

The prepared sample, such as by the addition of one or more markers to the collected blood sample, can then be transferred to the electrophoresis section 820 of the cartridge 800. The electrophoresis section 820 can be in fluid communication with the sample chamber 810 to allow the prepared sample to be transferred for testing purposes. One or more flow controls can be used to control the flow of the prepared sample between the chamber 810 and section 820. The flow can be controlled by a reader when the cartridge 800 is placed therein. Alternatively, other sources, such as a user or the cartridge 800 itself can control the flow of the treated sample.

The electrophoresis section 820 of the cartridge 800 includes an electrophoresis strip 822 and electrodes 824 and 826 disposed at either end. In the example shown in FIG. 8, an electrophoresis test is in process or completed as evidenced by the displayed banding. Prior to the initiation of the test, a buffer can be applied to the electrophoresis strip 822, such as by a buffer solution stored in the sample chamber 810, the electrophoresis section 820, a reader or another source. Alternatively, the electrophoresis strip 822 can have a buffer pre-applied, such as during a manufacturing process of the cartridge 800, by a user prior to a test or from another source. In a further embodiment, as described previously, the electrophoresis strip 822 can have a portion of the buffer applied in dry state, such as during a manufacturing process, that can be hydrated by the addition of a dilutant, such as deionized water, prior to the electrophoresis process to wet the electrophoresis strip 822 in a buffer solution.

The blood sample, treated or untreated, can be transferred from the sample chamber 810 and a measured portion can be deposited onto the electrophoresis strip 822 in a controlled manner at an initial position 830. Once the blood sample has been deposited on the electrophoresis strip 822, a voltage can be applied to/across the electrophoresis strip 822 using the electrodes 824 and 826. One electrode is positively charged and the other is negatively charged, creating a voltage and causing current to flow between the two electrodes 824, 826. The voltage/current between the electrodes 824, 826 causes portions of the deposited blood sample to move across the electrophoresis strip 822 at varying rates due to physical, electrical and/or chemical properties of each of the portions. The voltage/current is applied at a set or varying rate for a set amount of time to complete the test.

As shown in FIG. 8, the blood sample has separated into 4 distinct bands 832, 834, 836 and 838. Each band corresponds to a particular compound/component of the blood sample and the compounds/components can be identified based on their movement along the electrophoresis strip 822. Additionally, markers 840a and 840b were included in the deposited blood sample to assist with the band analysis/evaluation. In the example shown, marker 840a is positioned between bands 832 and 834. The positioning of marker 840a between the two bands 832, 834 can assist with differentiating each of the bands 832, 834 during analysis/evaluation of the band data. The other marker 840b is shown positioned with band 838. Marker 840b was selected to have the same electrophoresis properties as the compound/component associated with band 838, such that the marker 840b and band 838 would progress along the electrophoresis strip 822 together. Marker 840b can assist with determining the location of the band 838 and the distance the band has moved from the initial point 830. Markers can be selected based on their movement along the electrophoresis strip relative to the one or more compounds/components of the blood sample. In an embodiment, the markers can be selected to move with the one or more components/compounds of the blood sample, move separate from the one or more components/compounds of the blood sample (i.e., move at a different rate), or a combination thereof. While the bands are shown as distinct lines in the example of FIG. 8, in actuality each band will have a width and often decreasing intensity along that width, much like the tail of a brushstroke.

An optical imaging device 850 can image the electrophoresis strip 822 along with the bands 832, 834, 836, 838 and markers 840a, 840b present along its length. Using the captured image data, the optical imaging device, or another system/device such as a reader, can analyze the image to identify the compounds/components associated with each of the bands 832, 834, 836, 838 and their relative proportions. The captured image data can be used to determine a location of each of the bands 832, 834, 836, 838 and an intensity associated with each band. The intensity of the band can be calculated from the image data or can be determined using alternative methods, such as measuring a light transmission through the electrophoresis strip 822 and bands 832, 834, 836, 838 thereon. By plotting the intensity and position information, the proportion of each of the compounds/components represented by the bands 832, 834, 836, 838 can be determined by determining an area under the curve for each of the bands 832, 834, 836, 838 represented on the plot.

To assist with accurate analysis of the blood sample, a known sample quantity can be collected and/or used for analysis using an electrophoresis analysis process. The electrophoresis results indicate a relative proportion of one or more components/compounds present within the sample. Using the known sample quantity and the proportions, the actual amounts, or estimates thereof, of each of the one or more components/compounds present within the patient sample can be determined.

Imaging of the electrophoresis strip 822 and the bands and markers thereon can be performed using a set or varying spectrum of light and/or optical imaging devices and techniques, to capture a variety of information for use in analysis of the bands. In various lighting conditions and spectrums, different aspects of the bands can be more easily ascertained, such as band position and intensity. Additionally, the markers can be selected to fluoresce in certain lighting conditions, making it easier to determine a position of a marker relative to a band on the electrophoresis strip 822. Multiple captured images can be composited and/or used for the analysis process to increase the effectiveness and/or accuracy of the band analysis/evaluation.

In an alternative embodiment, the imaging of the electrophoresis strip 822 and the bands thereon can be performed using a generic optical imaging device, such as a digital camera. The cartridge 800 can be imaged using the digital camera, such as by a cell phone camera, and the captured image can be transferred to a device and/or system for analysis and/or evaluation. Such functionality can also be a secondary analysis/evaluation, or verification, method to support the optical imaging module/device of a reader.

Figure 9:
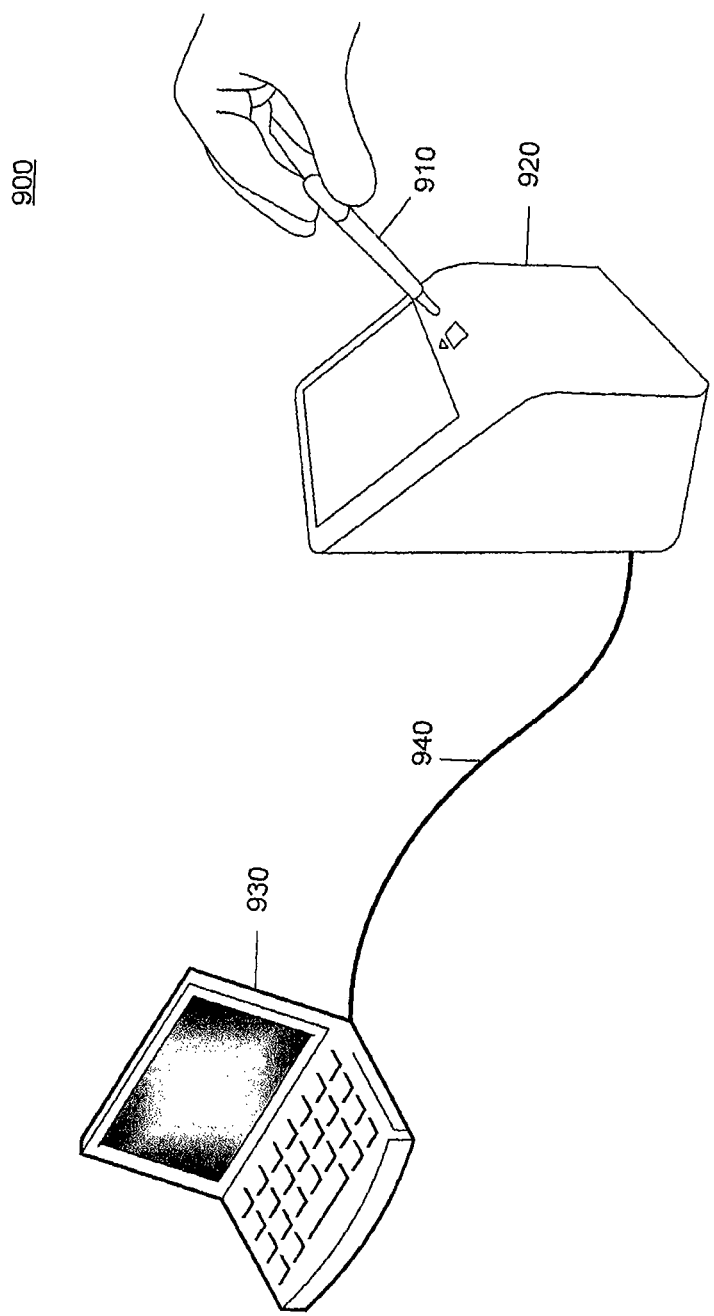
FIG. 9 illustrates a further example diagnostic system.

FIG. 9 illustrates an example diagnostic system 900 that includes a cartridge 910 and reader 920, such as described herein, the reader connected 940 to an external device 930, such as a computing device, including a laptop, phone, tablet, a server, remote computer, or other external device. The connection 940 between the reader 920 and the external device 930 can be a physical connection, such as a universal serial bus (USB) connector, such as shown in FIG. 9, or can be a wireless connection, such as an IR, Bluetooth® and/or WiFi electrical coupling, or a combination thereof. The connection 940 allows communication between the reader 920 and the external device 930. In an example, the reader 920 can perform analysis of a patient sample contained within the cartridge 910, data from the various analysis systems and/or elements of the reader 920 can be transmitted through the connection 940 to the external device 930 for processing. The external device 930 can then display or transmit the processed results, or portion thereof, to a user and/or can optionally transmit the processed results back to the reader 920 for display and/or transmission of the analysis results, or a portion thereof, to the user. In a further example, the reader 920 and external device 930 can both process all or a portion of the patient sample analysis data. The external device 930 can also control one or more aspects of the reader 920, such as the analysis able to be performed by the reader 920, authorized users of the reader 920 or other aspects of the reader 920 and its performance. Additionally, the external device 930 can be in the proximity of the reader 920, such as nearby, or can be remote from the reader 920, such as in another room or in another location including in another country. The external device 930 can communicate with and/or be connected to multiple readers and or other external systems, such as remote servers or databases.

Figure 10:
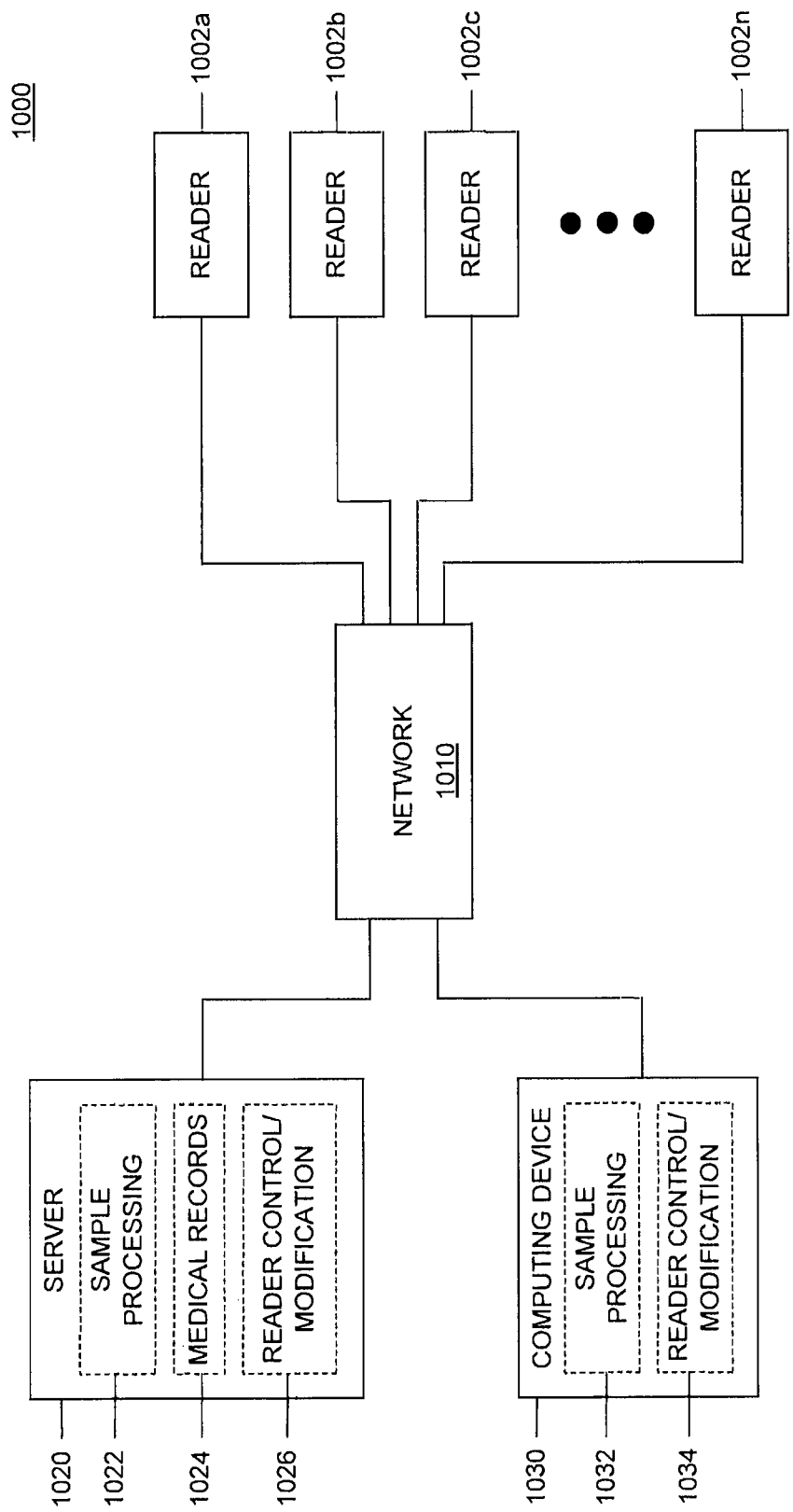
FIG. 10 is an example reader network.

FIG. 10 is an example reader network 1000. Various reader devices 1002*a*, 1002*b*, 1002*c* . . . 1002*n* are connected to external devices and/or systems, such as a server 1020 and/or computing device 1030, by a network 1010. The readers 1002*a*, 1002*b*, 1002*c* . . . 1002*n* can send and/or receive data, instructions, and other information to and/or from the external devices and/or systems 1020, 1030. The network 1010 can include physical and/or electronic connections to facilitate communication from the readers 1002*a*, 1002*b*, 1002*c* . . . 1002*n* to the external devices and/or systems 1020, 1030.

The readers 1002*a*, 1002*b*, 1002*c* . . . 1002*n* can be readers for use with a cartridge, as previously discussed, or can include other diagnostic and/or patient sample processing or storage devices. The readers 1002*a*, 1002*b*, 1002*c* . . . 1002*n* can communicate with the external devices and/or systems 1020, 1030 to transmit analysis data, receive analysis results and/or information, transmit status information, receive instructions, receive software updates and/or other communications or information exchanged between one or more readers 1002*a*, 1002*b*, 1002*c* . . . 1002*n* and/or external devices and/or systems 1020, 1030. The readers 1002*a*, 1002*b*, 1002*c* . . . 1002*n* can include a communication module to connect the reader 1002*a*, 1002*b*, 1002*c* . . . 1002*n* to the network 1010. The communication module can also be an external device to which the reader 1002*a*, 1002*b*, 1002*c* . . . 1002*n* is connected.

Additionally, the readers 1002*a*, 1002*b*, 1002*c* . . . 1002*n* can communicate with one another directly through a physical or wireless electronic connection. The connection between readers 1002*a*, 1002*b*, 1002*c* . . . 1002*n* can include intervening network devices, such as a router, or can be direct from one reader to one or more readers, such as an ad-hoc or local network. A reader can be designated as a primary device to transmit instructions to and receive data from other readers designated as secondary. Alternatively, no priority can be established between the readers 1002*a*, 1002*b*, 1002*c* . . . 1002*n*. The readers 1002*a*, 1002*b*, 1002*c* . . . 1002*n* can perform the same and/or different patient sample analyses.

The network 1010 can include wired connections, such as through an Ethernet connection, fiber optic connection, and/or other physical cable or connection. The network 1010 can also include electronic communication protocols, systems and/or methods, such a satellite communication, microwave communication, Wi-Fi, and Bluetooth®. The network 1010 can include multiple communication devices and/or protocols to facilitate communication between one or more readers 1002*a*, 1002*b*, 1002*c* . . . 1002*n* and/or external devices and/or systems 1020, 1030.

An example external device and/or system can include one or more servers 1020 which can be remote from or local to the readers 1002*a*, 1002*b*, 1002*c* . . . 1002*n*. The server 1020 can include sample processing 1022, medical records 1024, reader control/modification 1026 and/or other information or systems to communicate with and/or receive information from a reader 1002*a*, 1002*b*, 1002*c* . . . 1002*n*.

Sample processing 1022 can include receiving data from a reader 1002a, 1002b, 1002c . . . 1002n and analyzing the data to perform the analysis of the patient sample. Remote processing of the patient sample data can reduce the computing burden of the reader 1002a, 1002b, 1002c . . . 1002n. Additionally, remote processing can allow for more effective and efficient processing by consolidating the analysis in one or more locations, such as the server 1020. Consolidation can allow for the use of computer learning and/or larger databases for use in analysis of the patient sample. Such data aggregation can be used to map and/or research trends, map the progression of disorders and/or various other data analyses. Additionally, updating the analysis process can be required at fewer locations, the server 1020, rather than on each individual reader 1002a, 1002b, 1002c . . . 1002n.

The server 1020 can also include medical records 1024. The analysis performed by the server 1020 or reader 1002a, 1002b, 1002c . . . 1002n can be appended to the relevant patient medical record 1024. Medical records 1024 can be stored on the server 1020 or on an external device and/or system, to which the server 1020 and/or reader 1002a, 1002b, 1002c . . . 1002n can communicate the necessary data and/or analysis. The sample processing 1022 can also access the medical records 1024 to perform pattern analysis to determine trends, clusters, and potential preventative measures to reduce impact of a disease and/or condition in a certain region, population and/or demographic. Further, the pattern analysis can be used to determine spread of a disease and/or migration of a condition.

The server 1020 can also include reader control/modification 1026. Reader control/modification 1026 can include reader calibration information, software updates to the reader 1002a, 1002b, 1002c . . . 1002n, ensuring proper and/or authorized use of a reader 1002a, 1002b, 1002c . . . 1002n and/or other control or operational changes to a reader 1002a, 1002b, 1002c . . . 1002n. Centralizing reader control/modification 1026 can assist with proper reader 1002a, 1002b, 1002c . . . 1002n usage, maintenance and/or functionality to provide efficient and effective patient sample analysis using a reader 1002a, 1002b, 1002c . . . 1002n.

Another example external device and/or system can include one or more computing devices 1030. The computing device 1030, such as a mobile phone, computer, tablet, or other device, can be connected to one or more readers 1002a, 1002b, 1002c . . . 1002n through the network 1010. The computing device 1030 can receive information from the reader 1002a, 1002b, 1002c . . . 1002n and perform some or all the sample processing and/or analysis 1032, based on the received information. Additionally, the external device 1030 can act as an output to which the reader 1002a, 1002b, 1002c . . . 1002n transmits results, data and/or information regarding the patient sample analysis. As with the server, discussed above, the computing device 1030 can also include reader control/modification 1034. The reader control/modification 1034 can provide an input through which instruction to a reader 1002a, 1002b, 1002c . . . 1002n can be entered. Additionally, the reader control/modification 1034 can include calibration and/or maintenance data and/or processes a user and/or reader 1002a, 1002b, 1002c . . . 1002n can perform to assist with maintenance and/or calibration of the reader 1002a, 1002b, 1002c . . . 1002n. The proper functioning and calibration of the reader 1002a, 1002b, 1002c . . . 1002n can assist with the efficient and effective analysis of patient samples. Additionally, the computing device 1030 can communicate with the server 1020 using the network 1010 or other communication means, systems and/or processes.

In an example, the computing device 1030 can store and/or transmit data from one or more readers 1002a, 1002b, 1002c . . . 1002n to the server 1020. The data transmission can be in real-time or can be stored and transmitted when convenient or the computing device 1030 is again connected to a network 1010. Additionally, the computing device 1030 can transmit the results of an analysis to a patient and/or a patient representative, such as a patient's physician. As with transmission of the data from the reader, the transmission of the patient analysis can be performed in real-time or at a later time, such as when the computing device 1030 is again connected to a network 1010.

One of the functions of the reader network 1000 can include the sharing of the unique cartridge identifications of each of the cartridges analyzed by the readers 1002a, 1002b 1002c . . . 1002n of the network 1000. Sharing the identification of each of the previously used cartridges can prevent the unauthorized reuse of a cartridge. Each reader 1002a, 1002b 1002c . . . 1002n can query the server 1020, computing device 1030 and/or other readers to determine if a cartridge has been previously used as part of a cartridge verification process. In an embodiment, a list of cartridge identifications associated with previously used cartridges can be provided regularly to the reader 1002a, 1002b 1002c . . . 1002n, such as by the server 1020 or computing device 1030 via the network 1010, to update the cartridge verification system of the reader 1002a, 1002b 1002c . . . 1002n to prevent reuse of cartridges. Alternatively, or additionally, a list of cartridge identifications associated with unused cartridges can be provided regularly to the reader 1002a, 1002b 1002c . . . 1002n to assist with cartridge verification.

The invention claimed is:

1. A point-of-care diagnostic system, comprising:
a cartridge having:
  a sample chamber that is structured to receive a sample, the sample containing one or more component types, and also configured to store the sample within the sample chamber;
  an electrophoresis strip structured to receive at least a portion of the sample from the sample chamber and to receive a selectively applied electric current;
a reader having:
  a cartridge receptacle shaped to receive the cartridge and initiate an electrophoresis diagnostic process in response to receiving the cartridge;
  an electrophoresis module structured to cause the selectively applied electric current to be applied to the electrophoresis strip of the cartridge, the electrophoresis strip having thereon received at least a portion of the sample;
  an electrophoresis band detection module structured to detect one or more bands of at least a portion of the sample on the electrophoresis strip caused by the selectively applied electric current and to generate band detection data based on the one or more bands of the at least a portion of the sample;
a processor programmed to:
  receive the band detection data;
  analyze the band detection data to determine one or more band characteristics for each of the one or more bands, each of the one or more bands corresponding to one of the one or more component types of the sample;
  identify the one more component types of the sample based on the one or more band detection characteristics of each of the one or more bands;

generate diagnostic results based at least in part on the one or more component types of the sample; and transmit the diagnostic results to an output.

2. The point-of-care diagnostics system of claim 1, wherein the sample is a biological sample.

3. The point-of-case diagnostics system of claim 1, wherein the sample is a non-biological sample.

4. The point-of-case diagnostics system of claim 1, wherein the one or more component types includes a protein.

5. The point-of-care diagnostics system of claim 1, wherein the cartridge further includes at least one of a pre-loaded marker or buffer stored in one or more of the sample chamber, a treatment chamber in fluid communication with the sample chamber, or a marker-buffer chamber in fluid communication with the sample chamber, the treatment chamber or the marker-buffer chamber located within one or the other of the cartridge and the reader or integrated within the sample chamber.

6. The point-of-care diagnostics system of claim 5, further comprising one or both of a passive and an active mechanism that, when actuated, automatically causes one or more of the pre-loaded marker to mix with the sample or the buffer to be applied to the electrophoresis strip.

7. The point-of-care diagnostics system of claim 5, wherein one or the other of the reader and the cartridge further include a mixing chamber in which the pre-loaded marker is mixed with the sample.

8. The point-of-care diagnostics system of claim 1, wherein one or the other of the reader and the cartridge further include a sample depositor configured to selectively deposit a portion of the sample to the electrophoresis strip in a controlled manner.

9. The point-of-care diagnostics system of claim 8, wherein the controlled manner includes a pre-determined volume of the sample and pre-determined deposit area having a defined shape.

10. The point-of-care diagnostics system of claim 1, wherein the electrophoresis module includes electrodes that contact the electrophoresis strip of the cartridge after the cartridge is inserted in the reader.

11. The point-of-care diagnostics system of claim 1, further comprising one or both of:
an actuator that is positioned to be actuated when the cartridge is received in the cartridge receptacle, and
a cartridge sensor that is configured to detect the presence of the cartridge within the cartridge receptacle, the cartridge sensor electrically coupled to the processor and configured to transmit cartridge data indicating the presence of the cartridge in the cartridge receptacle to the processor.

12. The point-of-care diagnostics system of claim 1, wherein the electrophoresis module is further structured to stain the electrophoresis strip.

13. The point-of-care diagnostics system of claim 1, wherein the processor is further programmed to automatically generate the diagnostic results.

14. The point-of-care diagnostics system of claim 1, wherein the processor is further programmed to transmit the diagnostic results to a display.

15. The point-of-care diagnostics system of claim 14, wherein the processor is further programmed to receive user input requesting the diagnostic results and, based on the received user input, is also further configured to transmit the output interpretive data to the display.

16. The point-of-care diagnostics system of claim 14, wherein the display is integrated into the reader.

17. The point-of-care diagnostics system of claim 14, wherein the display is integrated into a remote computing device.

18. The point-of-care diagnostics system of claim 1, wherein a portion or all of one or both of the cartridge and the reader are temperature-controlled.

19. The point-of-care diagnostics system of claim 1, further comprising an integrated power source in the reader, the power source electrically coupled to the electrophoresis module, the electrophoresis band detection module and the processor.

20. The point-of-care diagnostics system of claim 1, further comprising an output configured to receive the diagnostic results, and the output is integrated within the reader and includes one or more of a display, a visual indicator, an audible indicator, and a computing element remote from the reader.

21. The point-of-care diagnostics system of claim 20, wherein the remote computing element is wirelessly connected to the reader or is connected to the reader via a wired electrical connection.

22. The point-of-care diagnostics system of claim 1, wherein the processor includes processing circuitry that is integrated within the reader or at least a portion of the processing circuitry is integrated within the cartridge.

23. The point-of-care diagnostics system of claim 1, wherein the processor includes processing circuitry that is wirelessly connected to the electrophoresis band detection module and is integrated partially or entirely in a computing element remote from the reader.

24. The point-of-care diagnostics system of claim 1, wherein the processor is further programmed to determine the relative proportions of the one or more component types in the sample and to generate the diagnostic results based at least in part on the relative proportions of the one or more component types in the sample.

25. The point-of-care diagnostics system of claim 1, further comprising an actuator electrically coupled to the processor, the actuator being structured to indicate that the cartridge is received within the cartridge receptacle, and the processor being further programmed to transmit instructions to the electrophoresis module to begin applying a voltage to the electrophoresis strip in response to the actuator indicating that the cartridge is received within the cartridge receptacle.

26. The point-of-care diagnostics system of claim 1, wherein the processor is further programmed to measure the spacing from the application point and between each of the bands, and to generate the diagnostic results to include the measurement of the spacing between each of the bands.

27. The point-of-care diagnostics system of claim 1, wherein the processor is further programmed to:
analyze the received band detection data to identify the one more component types of the sample and determine the relative proportions of the one or more component types in the sample,
automatically generate the diagnostic results that indicates the one or more component types of the sample and relative proportions of the one or more component types of the sample based on the received band detection data, and
output the diagnostic results.

28. The point-of-care diagnostics system of claim 27, wherein the processor is further programmed to transmit the diagnostic results to one or both of a display integrated in the reader and a remote computing system.

29. The point-of-care diagnostics system of claim 1, wherein the processor is further programmed to automatically analyze the received band detection data to measure the spacing to and between each of the bands and to generate the diagnostic results to include the measured spacing of each of the bands.

30. The point-of-care diagnostics system of claim 1, wherein the one or more band detection characteristics include an intensity and location for each of the one or more bands and the processing circuitry is further configured to correlate the band detection data of the sample with a level of each of the component types of the sample.

* * * * *

UNITED STATES PATENT AND TRADEMARK OFFICE
CERTIFICATE OF CORRECTION

PATENT NO. : 10,375,909 B2
APPLICATION NO. : 16/113261
DATED : August 13, 2019
INVENTOR(S) : Peter Galen et al.

Page 1 of 1

It is certified that error appears in the above-identified patent and that said Letters Patent is hereby corrected as shown below:

In the Claims

Column 34, Line 55, Claim 27, "one more component", should be -- one or more component --

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*